(12) United States Patent
Seomoon et al.

(10) Patent No.: US 11,961,322 B2
(45) Date of Patent: *Apr. 16, 2024

(54) FORCE SENSOR HAVING FORCE SENSOR ELECTRODES, DISPLAY DEVICE INCLUDING THE SAME, AND METHOD FOR DRIVING THE SAME

(71) Applicant: Samsung Display Co., LTD., Yongin-si (KR)

(72) Inventors: Hee Seomoon, Hwaseong-si (KR); Won Ki Hong, Suwon-si (KR); Hyeon Jun Lee, Seoul (KR)

(73) Assignee: Samsung Display Co., Ltd., Yongin-si (KR)

( * ) Notice: Subject to any disclaimer, the term of this patent is extended or adjusted under 35 U.S.C. 154(b) by 268 days.

This patent is subject to a terminal disclaimer.

(21) Appl. No.: 17/189,203

(22) Filed: Mar. 1, 2021

(65) Prior Publication Data

US 2021/0319198 A1 Oct. 14, 2021

(30) Foreign Application Priority Data

Apr. 10, 2020 (KR) ........................ 10-2020-0043740

(51) Int. Cl.
*G06V 40/13* (2022.01)
*A61B 5/0265* (2006.01)
*G06F 1/16* (2006.01)

(52) U.S. Cl.
CPC ........ *G06V 40/1318* (2022.01); *A61B 5/0265* (2013.01); *G06F 1/1684* (2013.01); *A61B 2562/0261* (2013.01)

(58) Field of Classification Search
CPC .............. G06V 40/1318; A61B 5/0265; A61B 2562/0261; A61B 5/6843; A61B 5/6898;
(Continued)

(56) References Cited

U.S. PATENT DOCUMENTS

| 4,782,336 A | * 11/1988 | Bailey ...................... G09F 9/33 345/55 |
| 9,049,998 B2 | 6/2015 | Brumback et al. |

(Continued)

FOREIGN PATENT DOCUMENTS

| JP | 2022172220 A | * 11/2022 | ........... A61B 5/0022 |
| KR | 2019-0125554 | 11/2019 | |

(Continued)

OTHER PUBLICATIONS

Sang Yong Lee. "Development of a High Performance Medical Blood Pressure Measurement System" with English Abstract.

*Primary Examiner* — David D Davis
(74) *Attorney, Agent, or Firm* — H.C. Park & Associates, PLC

(57) ABSTRACT

Provided are a force sensor, a display device including the same, and a method of driving the same. The force sensor includes a first base substrate and a second base substrate facing each other; first force sensor electrodes extending in a first direction and arranged in a second direction crossing the first direction on the first base substrate; second force sensor electrodes extending in the second direction and arranged in the first direction on the second base substrate; and a sensor hole configured to transmit light. Any one of the first force sensor electrodes includes a first sub-force sensor electrode disposed on a first side of the sensor hole and a second sub-force sensor electrode disposed on a second side opposite to the first side of the sensor hole.

30 Claims, 33 Drawing Sheets

(58) Field of Classification Search
CPC ... A61B 5/022; A61B 5/0261; A61B 5/02233; A61B 5/02255; A61B 5/02108; A61B 2562/0247; G06F 1/1684; G06F 1/1637; G06F 1/1686; G06F 3/044; G09F 9/301; G09F 9/33; G01L 9/0072; G01L 1/144
See application file for complete search history.

(56) References Cited

U.S. PATENT DOCUMENTS

| | | | |
|---|---|---|---|
| 11,515,366 B2 * | 11/2022 | Hong | A61B 5/0053 |
| 2018/0017996 A1 * | 1/2018 | Ryu | G06F 1/1643 |
| 2019/0104997 A1 | 4/2019 | Kang et al. | |
| 2019/0117124 A1 * | 4/2019 | Hsu | A61B 5/6892 |
| 2019/0227603 A1 * | 7/2019 | Noh | G06F 1/1605 |
| 2020/0026335 A1 * | 1/2020 | Lee | G06F 1/1639 |
| 2020/0064968 A1 * | 2/2020 | Kim | G06F 3/0445 |
| 2020/0382739 A1 * | 12/2020 | Lu | G02F 1/133331 |
| 2021/0296408 A1 * | 9/2021 | Hong | G01L 5/22 |

FOREIGN PATENT DOCUMENTS

| | | |
|---|---|---|
| KR | 2019-0137192 | 12/2019 |
| KR | 10-2021-0117373 | 9/2021 |

\* cited by examiner

FIG. 30

| 264 | 210 | 188 | 88 | — PSC |
|-----|-----|-----|-----|-----|
| 267 | 184 |     | 120 | — SH |
| 226 | 198 | 273 | 146 | |
| 167 | 280 | 330 | 71 | |

FIG. 31

| 241 | 193 | 172 | 79  |
|-----|-----|-----|-----|
| 244 | 168 | 224 | 107 |
| 207 | 180 | 248 | 133 |
| 154 | 257 | 312 | 68  |

—PSC

FORCE SENSOR HAVING FORCE SENSOR ELECTRODES, DISPLAY DEVICE INCLUDING THE SAME, AND METHOD FOR DRIVING THE SAME

CROSS-REFERENCE TO RELATED APPLICATION

This application claims priority from and the benefit of Korean Patent Application No. 10-2020-0043740, filed on Apr. 10, 2020, which is hereby incorporated by reference for all purposes as if fully set forth herein.

BACKGROUND

Field

Exemplary embodiments of the invention relate generally to a force sensor, a display device including the same, and a method of driving the same.

Discussion of the Background

A display device is a device that displays a screen, and has been used not only for a television and monitor, but also for a portable smartphone, tablet personal computer (PC) and the like. In the case of a portable display device, various functions are included in the display device. For example, a camera and a fingerprint sensor may be included in the display device.

Recently, as the healthcare industry is in the spotlight, methods have been developed to more easily obtain biometric information related to health. For example, attempts have been made to replace a traditional blood pressure measuring device such as an oscillometric device with a portable blood pressure measuring device. However, the portable blood pressure measuring device itself requires a separate light source, sensor, and display, and it is necessary to separately carry the portable blood pressure measuring device in addition to the portable smartphone or tablet pc, which causes inconvenience.

The above information disclosed in this Background section is only for understanding of the background of the inventive concepts, and, therefore, it may contain information that does not constitute prior art.

SUMMARY

Devices constructed according to exemplary embodiments of the invention are capable of sensing a force.

According to one or more implementations of the invention, a display device includes display device capable of measuring a blood pressure using a force sensor capable of sensing a force.

Exemplary embodiments also provide a method of driving a force sensor capable of sensing a force.

Additional features of the inventive concepts will be set forth in the description which follows, and in part will be apparent from the description, or may be learned by practice of the inventive concepts.

A force sensor according to an exemplary embodiment includes a first base substrate and a second base substrate facing each other; first force sensor electrodes extending in a first direction and arranged in a second direction crossing the first direction on the first base substrate; second force sensor electrodes extending in the second direction and arranged in the first direction on the second base substrate; and a sensor hole configured to transmit light. Any one of the first force sensor electrodes includes a first sub-force sensor electrode disposed on a first side of the sensor hole and a second sub-force sensor electrode disposed on a second side opposite to the first side of the sensor hole.

A display device according to an exemplary embodiment includes a display panel including a display area having pixels configured to display an image, a force sensor disposed on one surface of the display panel to sense a force applied from an outside, and including a sensor hole which transmits light in a thickness direction of the display panel; and an optical sensor disposed to overlap the sensor hole in the thickness direction of the display panel and configured to sense light incident through the sensor hole.

A method of driving a force sensor capable of sensing a force according to an exemplary embodiment includes applying driving signals to the first force sensor electrodes, and detecting sensing signals from the second force sensor electrodes; analyzing the sensing signals to calculate force values of force sensing cells disposed in crossing regions of the first force sensor electrodes and the second force sensor electrodes, respectively; and calculating a force value of the sensor hole using the force values.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

FIGS. 30 and 31 are exemplary views illustrating force values sensed in force sensing cells of a force sensor according to the presence or absence of a hole.

DETAILED DESCRIPTION

Figure 1:
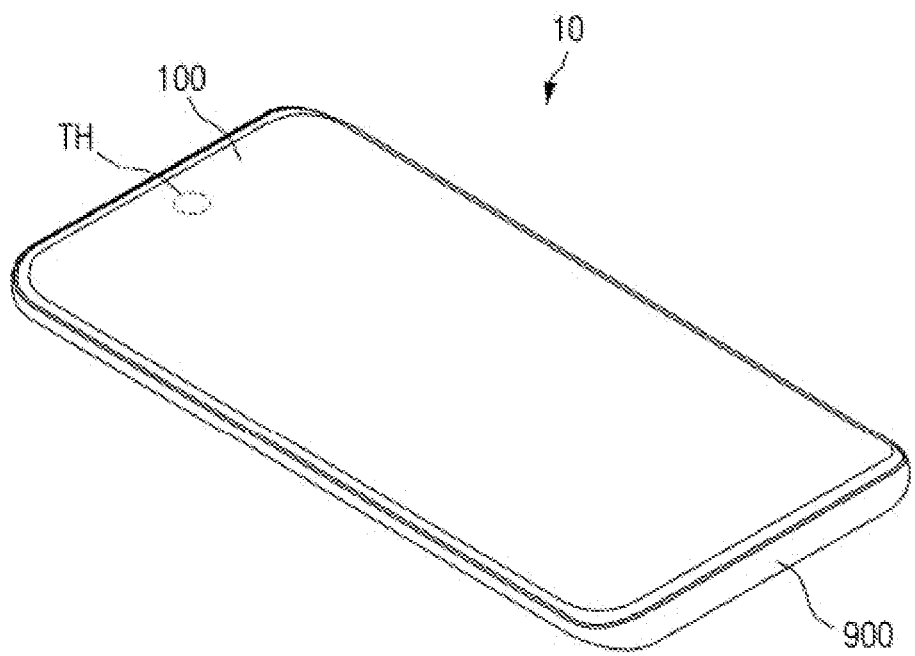
FIG. 1 is a schematic perspective view illustrating a display device according to an exemplary embodiment of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are illustrated in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side"

(e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Figure 2:
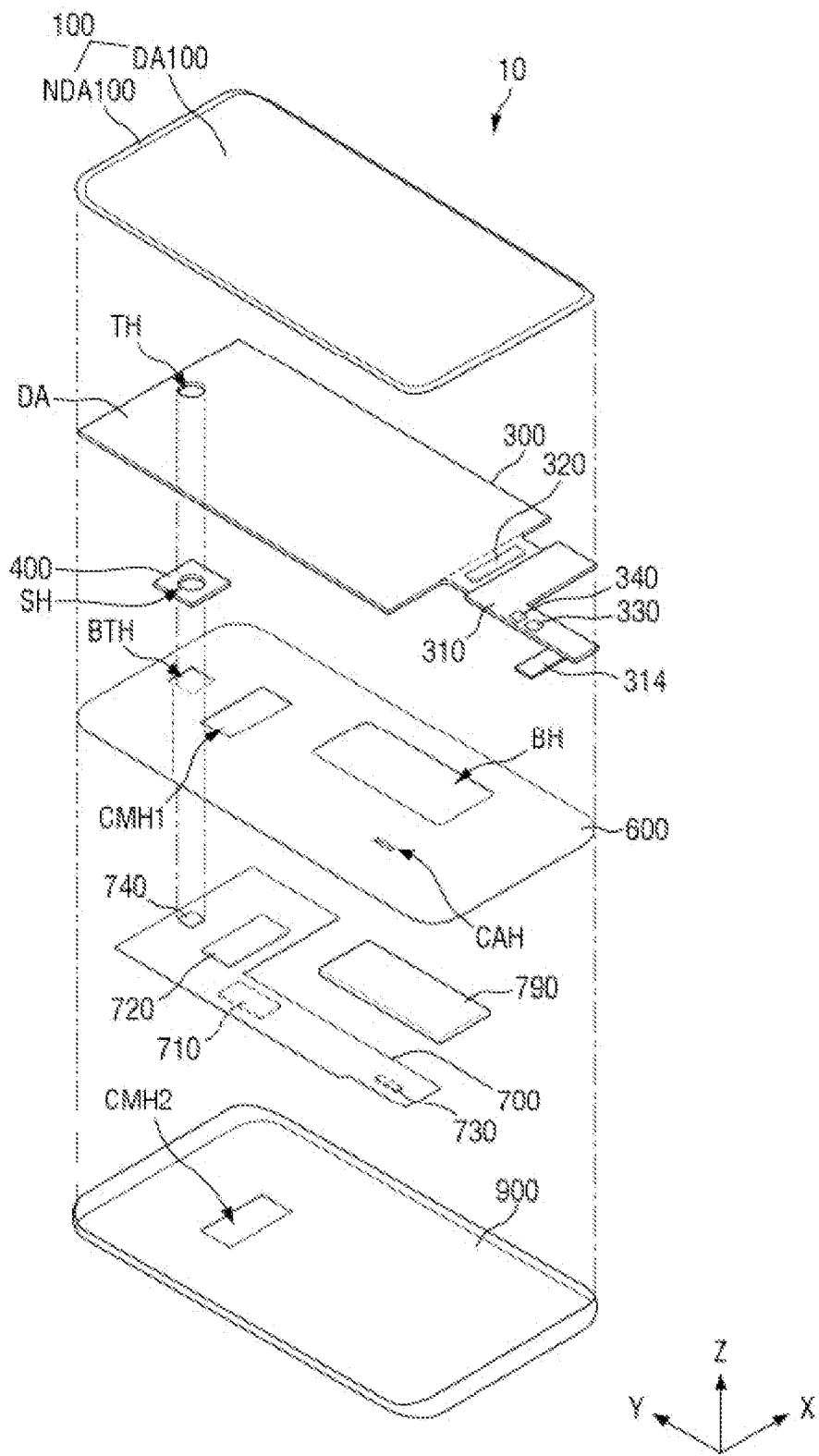
FIG. 2 is an exploded perspective view illustrating a display device according to an exemplary embodiment of the invention.

FIG. 1 is a schematic perspective view illustrating a display device according to an exemplary embodiment. FIG. 2 is an exploded perspective view illustrating a display device according to an exemplary embodiment.

Referring to FIGS. 1 and 2, a display device 10 according to an exemplary embodiment may be applied to portable electronic devices such as a mobile phone, a smartphone, a tablet personal computer, a mobile communication terminal, an electronic organizer, an electronic book, a portable multimedia player (PMP), a navigation system, an ultra mobile PC (UMPC) or the like. Alternatively, the display device 10 according to an exemplary embodiment may be applied as a display unit of a television, a laptop, a monitor, a billboard, or an Internet-of-Things (IoT) terminal. Alternatively, the display device 10 according to an exemplary embodiment may be applied to wearable devices such as a smart watch, a watch phone, a glasses type display, or a head mounted display (HMD). Alternatively, the display device 10 according to an exemplary embodiment may be applied to a dashboard of a vehicle, a center fascia of a vehicle, a center information display (CID) disposed on a dashboard of a vehicle, a room mirror display in place of side mirrors of a vehicle, or a display disposed on a rear surface of a front seat for rear seat entertainment of a vehicle.

In the inventive concepts, a first direction (X-axis direction) may be a short side direction of the display device 10, for example, a horizontal direction of the display device 10. A second direction (Y-axis direction) may be a long side direction of the display device 10, for example, a vertical direction of the display device 10. A third direction (Z-axis direction) may be a thickness direction of the display device 10.

The display device 10 may have a planar shape similar to a rectangular shape. For example, the display device 10 may have a planar shape similar to a rectangular shape having short sides in the first direction (X-axis direction) and long sides in the second direction (Y-axis direction), as illustrated in FIG. 1. The corner where the short side in the first direction (X-axis direction) and the long side in the second direction (Y-axis direction) meet may be rounded to have a predetermined curvature or may be right-angled. The planar shape of the display device 10 is not limited to a rectangular shape, and may be formed in a shape similar to other polygonal shapes, a circular shape, or elliptical shape.

The display device 10 may be formed flat. Alternatively, the display device 10 may be formed such that two sides facing each other are bendable. For example, the display device 10 may be formed such that the left and right sides are bendable. Alternatively, the display device 10 may be formed such that all of the upper, lower, left, and right sides are bendable.

The display device 10 according to an exemplary embodiment includes a cover window 100, a display panel 300, a display circuit board 310, a display driving circuit 320, a force sensor 400, a bracket 600, a main circuit board 700, an optical sensor 740 and a lower cover 900.

The cover window 100 may be disposed above the display panel 300 to cover the front surface of the display panel 300. Accordingly, the cover window 100 may be configured to protect the front surface of the display panel 300.

The cover window 100 may include a light transmitting portion DA100 corresponding to the display panel 300 and a light blocking portion NDA100 corresponding to an area other than the display panel 300. The light blocking portion NDA100 may be formed opaquely. Alternatively, the light blocking portion NDA100 may be formed as a decorative layer having a pattern that can be displayed to a user when an image is not displayed.

The display panel 300 may be disposed under the cover window 100. The display panel 300 may include a display area DA and a non-display area NDA (illustrated in FIG. 3). The display area DA may be an area including pixels displaying an image, and the non-display area NDA may be an area in which an image is not displayed as a peripheral area of the display area DA. The non-display area NDA may not include pixels. The non-display area NDA may be disposed to surround the display area DA as illustrated in FIG. 2, but is not limited thereto. The display area DA may occupy most of the area of the display panel 300.

The display panel 300 may include a through hole TH. The through hole TH may be a hole penetrating the display panel 300. The through hole TH may be arranged to be surrounded by the display area DA.

The through hole TH may overlap a sensor hole SH corresponding to the force sensor 400, a bracket hole BTH of the bracket 600, and the optical sensor 740 in the third direction (Z-axis direction). Therefore, light passing through the through hole TH of the display panel 300 may be incident on the optical sensor 740 through the sensor hole SH and the battery hole BH. Therefore, although the optical sensor 740 is disposed under the display panel 300, the optical sensor 740 may sense the light incident from the front surface of the display device 10.

Meanwhile, FIG. 2 illustrates the display panel 300 including one through hole TH, but the number of through holes TH is not limited thereto. A plurality of through holes TH may be disposed at different locations on the display panel 300. When the display panel 300 includes a plurality of the through holes TH, one of the through holes TH may overlap the sensor hole SH, the battery hole BH, and the optical sensor 740 in the third direction (Z-axis direction). The other through holes TH may overlap other sensor holes, other battery holes, and sensor units other than the optical sensor 740. The sensor units may be proximity sensors, illuminance sensors, or front camera sensors.

The display panel 300 may be a light emitting display panel including a light emitting element. For example, the display panel 300 may be an organic light emitting display panel using an organic light emitting diode including an organic light emitting layer, a micro light emitting diode display panel using a micro LED, a quantum dot light emitting display panel using a quantum dot light emitting diode including a quantum dot light emitting layer, or an inorganic light emitting display panel using an inorganic light emitting element including an inorganic semiconductor. Hereinafter, a case where the display panel 300 is an organic light emitting display panel will be mainly described.

Further, the display panel 300 may include a touch electrode layer having touch electrodes configured to sense an object such as a human finger, a pen or the like. In this case, the touch electrode layer may be disposed on a display layer in which pixels displaying an image are arranged. The display layer and the touch electrode layer will be specifically described later with reference to FIG. 8.

The display circuit board 310 and the display driving circuit 320 may be attached to one side of the display panel 300. The display circuit board 310 may be a flexible printed circuit board which is bendable, a rigid printed circuit board which is solid to be hardly bent, or a composite printed circuit board having both of the rigid printed circuit board and the flexible printed circuit board.

The display driving circuit 320 may receive control signals and power voltages through the display circuit board 310 to generate and output signals and voltages configured to drive the display panel 300. The display driving circuit 320 may be formed of an integrated circuit (IC) to be attached on the display panel 300 by a chip-on-glass (COG) method, a chip-on-plastic (COP) method, or an ultrasonic bonding method, but the inventive concepts are not limited thereto. For example, the display driving circuit 320 may be attached onto the display circuit board 310.

A touch driving circuit 330 and a force driving circuit 340 may be disposed on the display circuit board 310. Each of the touch driving circuit 330 and the force driving circuit 340 may be formed of an IC to be attached to the top surface of the display circuit board 310. Alternatively, the touch driving circuit 330 and the force driving circuit 340 may be integrally formed as one IC in some cases.

The touch driving circuit 330 may be electrically connected to the touch electrodes of the touch electrode layer of the display panel 300 through the display circuit board 310. The touch driving circuit 330 may output a touch driving signal to the touch electrodes and sense the voltage charged in the capacitances of the touch electrodes.

The touch driving circuit 330 may generate touch data according to the change in the electrical signal sensed at each of the touch electrodes to transmit the touch data to a main processor 710. Then, the main processor 710 may analyze the touch data to generate touch coordinates. The touch may include a contact touch and a proximity touch. The contact touch indicates that the object such as the human finger or pen makes a direct contact with the cover window disposed above the touch electrode layer. The proximity touch indicates that the object such as the human finger or pen is positioned above the cover window to be proximately apart therefrom, such as hovering.

The force driving circuit 340 may detect an electrical signal from a force sensor electrode of the force sensor 400, convert the detected signal into force data, and transmit it to the main processor 710. The main processor 710 may determine whether force has been applied to the force sensor 400 and may calculate the magnitude of the force applied to the force sensor 400 based on the force data.

Further, a power supply unit may additionally be disposed on the display circuit board 310 to supply display driving voltages configured to drive the display driving circuit 320.

The force sensor 400 may be disposed to overlap the display area DA of the display panel 300 in the third direction (Z-axis direction). The force sensor 400 may be disposed on one surface of the display panel 300. For example, the force sensor 400 may be disposed on the bottom surface of the display panel 300. In this case, the top surface of the force sensor 400 may be attached to the bottom surface of the display panel 300 via a transparent adhesive member. FIG. 2 illustrates that the force sensor 400 is disposed on the bottom surface of the display panel 300, but the inventive concepts are not limited thereto. The force sensor 400 may be disposed on the bottom surface of the bracket 600.

The bracket 600 may be disposed under the display panel 300. The bracket 600 may include plastic, metal, or both plastic and metal. The bracket 600 may include a first camera hole CMH1 into which a first camera sensor 720 is inserted, a battery hole BH in which a battery is disposed, a cable hole CAH through which a cable 314 connected to the display circuit board 310 passes, and a bracket hole BTH overlapping the optical sensor 740 in the third direction (Z-axis direction). In this case, the optical sensor 740 may be arranged in the bracket hole BTH. Alternatively, the bracket 600 may not include the bracket hole BTH, and in this case, the bracket 600 may be formed not to overlap the through hole TH of the display panel 300.

The main circuit board 700 and a battery 790 may be disposed under the bracket 600. The main circuit board 700 may be a printed circuit board or a flexible printed circuit board.

The main circuit board 700 may include a main processor 710, a first camera sensor 720, a main connector 730, and the optical sensor 740. The first camera sensor 720 may be disposed on both the top and bottom surfaces of the main circuit board 700, the main processor 710 may be disposed on the top surface of the main circuit board 700, and the main connector 730 may be disposed on the bottom surface of the main circuit board 700. The optical sensor 740 may be disposed on the top surface of the main circuit board 700.

The main processor 710 may control all functions of the display device 10. For example, the main processor 710 may output digital video data to the display driving circuit 320 through the display circuit board 310 such that the display panel 300 displays an image. Further, the main processor 710 may receive touch data from the touch driving circuit 330 and determine the user's touch coordinates, and then execute an application indicated by an icon displayed on the user's touch coordinates. Furthermore, the main processor 710 may convert first image data inputted from the first camera sensor 720 into digital video data and output it to the display driving circuit 320 through the display circuit board 310, thereby displaying an image captured by the first camera sensor 720 on the display panel 300. In addition, the main processor 710 may determine the user's blood pressure according to a sensor signal inputted from the optical sensor 740.

The first camera sensor 720 may process an image frame of a still image or video obtained by the image sensor and output it to the main processor 710. The first camera sensor 720 may be a complementary metal-oxide-semiconductor (CMOS) image sensor or a charge-coupled device (CCD) sensor. The first camera sensor 720 may be exposed to the bottom surface of the lower cover 900 by a second camera hole CMH2 to thereby capture an image of a background or an object disposed below the display device 10.

The cable 314 passing through the cable hole CAH of the bracket 600 may be connected to the main connector 730. Thus, the main circuit board 700 may be electrically connected to the display circuit board 310.

The optical sensor 740 may include a light receiving element capable of sensing light incident through the through hole TH. In this case, the light receiving element may be a photodiode or phototransistor. For example, the optical sensor 740 may be a CMOS image sensor or a CCD sensor which is capable of sensing light. The optical sensor 740 may output an optical signal to the main processor 710 according to the amount of light reflected from an object disposed above the through hole TH. The main processor 710 may generate a pulse wave signal reflecting a change in blood flow according to heartbeats, according to the optical signal. The main processor 710 may measure a blood pressure of the user according to the pulse wave signal. A method of measuring a blood pressure of a person using the optical sensor 740 will be described later with reference to FIGS. 4 and 5.

The battery 790 may be disposed so as not to overlap the main circuit board 700 in the third direction (Z-axis direction). The battery 790 may overlap the battery hole BH of the bracket 600.

In addition, the main circuit board 700 may be further equipped with a mobile communication module capable of transmitting and receiving radio signals with at least one of a base station, an external terminal, and a server in a mobile communication network. The wireless signal may include various types of data according to transmission and reception of a voice signal, a video call signal, or a text/multimedia message.

The lower cover 900 may be disposed below the main circuit board 700 and the battery 790. The lower cover 900 may be fixed by being fastened to the bracket 600. The lower cover 900 may form an external appearance of the bottom surface of the display device 10. The lower cover 900 may include plastic, metal, or both plastic and metal.

The second camera hole CMH2 exposing the bottom surface of the first camera sensor 720 may be formed in the lower cover 900. The position of the first camera sensor 720 and the positions of the first and second camera holes CMH1 and CMH2 corresponding to the first camera sensor 720 are not limited to the embodiment illustrated in FIG. 2.

Figure 3:
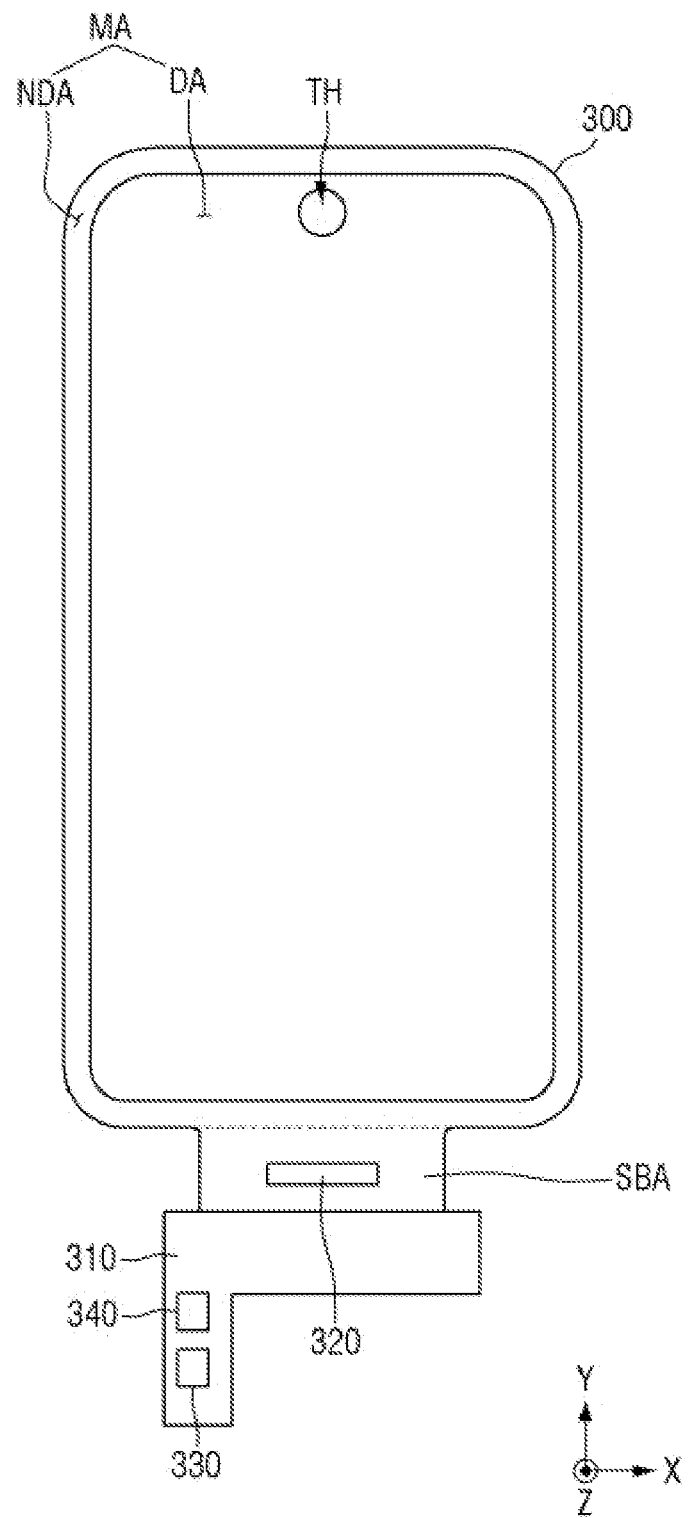
FIG. 3 is a plan view illustrating a display panel, a display circuit board, a display driving circuit, and a touch driving circuit according to an exemplary embodiment of the invention.

FIG. 3 is a plan view illustrating a display panel, a display circuit board, a display driving circuit, and a touch driving circuit according to an exemplary embodiment.

Referring to FIG. 3, the display panel 300 may be a rigid display panel which is rigid not to be easily bent, or a flexible display panel which is flexible to be easily bent, folded, or rolled up. For example, the display panel 300 may be a foldable display panel which can be folded and unfolded, a curved display panel having a curved display surface, a bended display panel having a bent area other than the display surface, a rollable display panel which can be rolled up and rolled out and a stretchable display panel which can be stretched.

Further, the display panel 300 may be a transparent display panel which is transparently implemented to allow an object or background disposed behind the rear surface of the display panel 300 to be viewed from the front surface of the display panel 300. Further, the display panel 300 may be a reflective display panel which is capable of reflecting an object or background in front of the front surface of the display panel 300.

The display panel 300 may include a main region MA and a sub-region SBA protruding from one side of the main region MA. The main region MA may include a display area DA displaying an image and a non-display area NDA that is a peripheral area of the display area DA. The display area DA may occupy most of the main region MA. The display area DA may be disposed at the center of the main region MA. The non-display area NDA may be an area outside the display area DA. The non-display area NDA may be defined as an edge area of the display panel 300.

The display panel 300 may include the through hole TH. The through hole TH may be a hole penetrating the display panel 300. FIG. 3 illustrates that the through hole TH is a hole penetrating the display panel 300, that is, a physically formed hole, but the inventive concepts are not limited thereto.

Because the through hole TH overlaps the optical sensor 740 in the third direction (Z-axis direction) as illustrated in FIG. 2, light passing through the through hole TH may be incident on the optical sensor 740. Accordingly, the optical sensor 740 may sense the light incident from the front surface of the display device 10 even though the optical sensor 740 is disposed to overlap the display panel 300 in the third direction (Z-axis direction). For example, the optical sensor 740 may sense light reflected from an object disposed above the through hole TH.

The through hole TH may be disposed to be surrounded by the display area DA. Alternatively, the through hole TH may be disposed to be surrounded by the non-display area NDA, or may be disposed between the display area DA and the non-display area NDA. In addition, although FIG. 2 illustrates that the through hole TH is disposed adjacent to the upper center of the display panel 300, the arrangement position of the through hole TH is not limited thereto.

The sub-region SBA may protrude in the second direction (Y-axis direction) from one side of the main region MA. As illustrated in FIG. 2, the length of the sub-region SBA in the first direction (X-axis direction) may be smaller than the length of the main region MA in the first direction (X-axis direction), and the length of the sub-region SBA in the second direction (Y-axis direction) may be smaller than the length of the main region MA in the second direction (Y-axis direction), but the inventive concepts are not limited thereto. The sub-region SBA may be foldable to be disposed under the display panel 300. In this case, the sub-region SBA may overlap the main region MA in the third direction (Z-axis direction).

The sub-region SBA of the display panel 300 may be foldable to be placed under the display panel 300. In this case, the sub-region SBA of the display panel 300 may overlap the main region MA of the display panel 300 in the third direction (Z-axis direction).

The display circuit board 310 and the display driving circuit 320 may be attached to the sub-region SBA of the display panel 300. The display circuit board 310 may be attached onto pads of the sub-region SBA of the display panel 300 using a low resistance and high reliability material such as an anisotropic conductive film, a self assembly anisotropic conductive paste (SAP) or the like. The touch driving circuit 330 may be disposed on the display circuit board 310.

Figure 4:
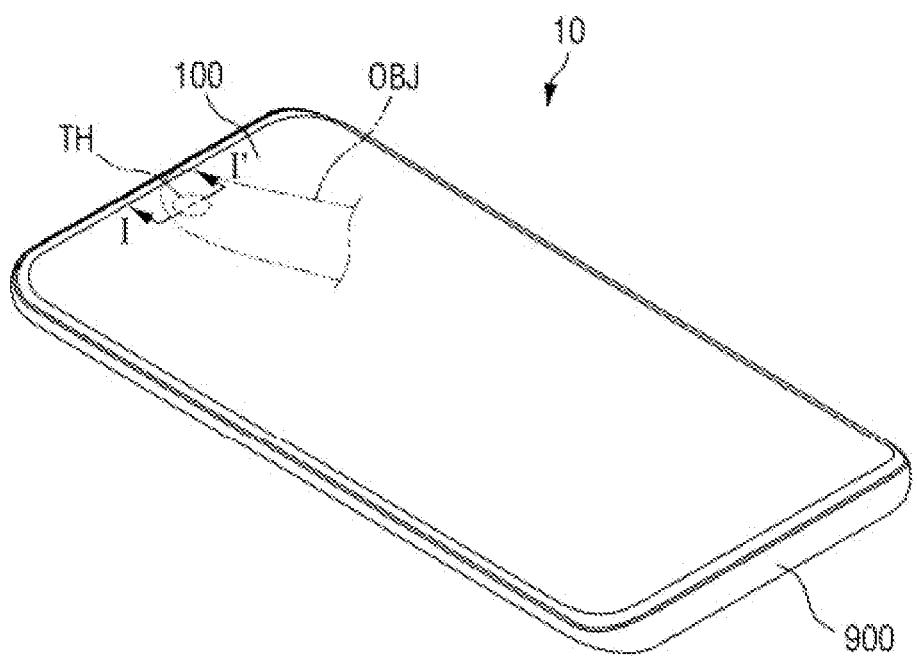
FIG. 4 is a schematic perspective view illustrating the display device measuring a blood pressure according to an exemplary embodiment of the invention.
Figure 5:
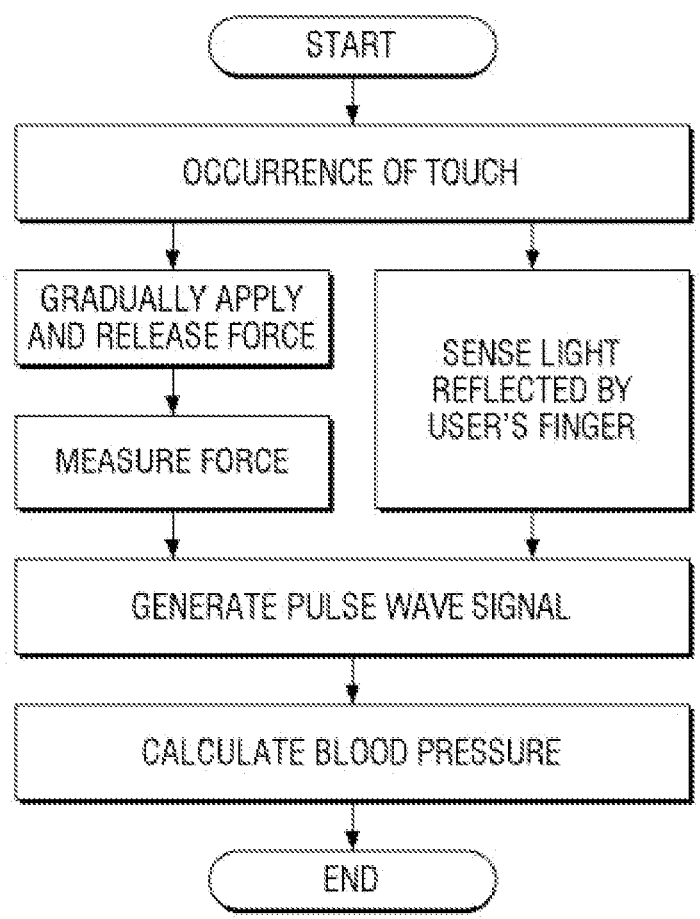
FIG. 5 is a flowchart illustrating a method of measuring a blood pressure by the display device according to an exemplary embodiment of the invention.

FIG. 4 is a schematic perspective view illustrating the display device measuring a biometric element such as blood pressure according to an exemplary embodiment. FIG. 5 is a flowchart illustrating a method of measuring a biometric element such as blood pressure by the display device according to an exemplary embodiment.

Referring to FIGS. 4 and 5, when a user's body part, for example, a finger OBJ touches the front surface of the display device 10, the display device 10 may recognize that a touch has occurred. The display device 10 may recognize the user's touch using the touch electrode layer of the display panel 300, or the force sensor 400.

When the display device 10 determines that a touch has occurred, the display device 10 may operate in a blood pressure measurement mode. For example, when the user sets the blood pressure measurement mode through a program or application of the display device 10 before measuring a blood pressure, the display device 10 may perform blood pressure measurement according to the touch occurrence. Alternatively, the display device 10 may be configured to automatically switch to the blood pressure measurement mode after a touch occurs without the user's additional action for mode determination. When the user touches a position that is out of the blood pressure measurement position, the display device 10 may operate in a touch mode. When the user touches a position that corresponds to the blood pressure measurement position, the display device 10 may operate in the blood pressure measurement mode. In addition, when the user increases a touch force, the display device 10 may operate in the blood pressure measurement mode by force analysis of the force sensor 400.

Figure 6:
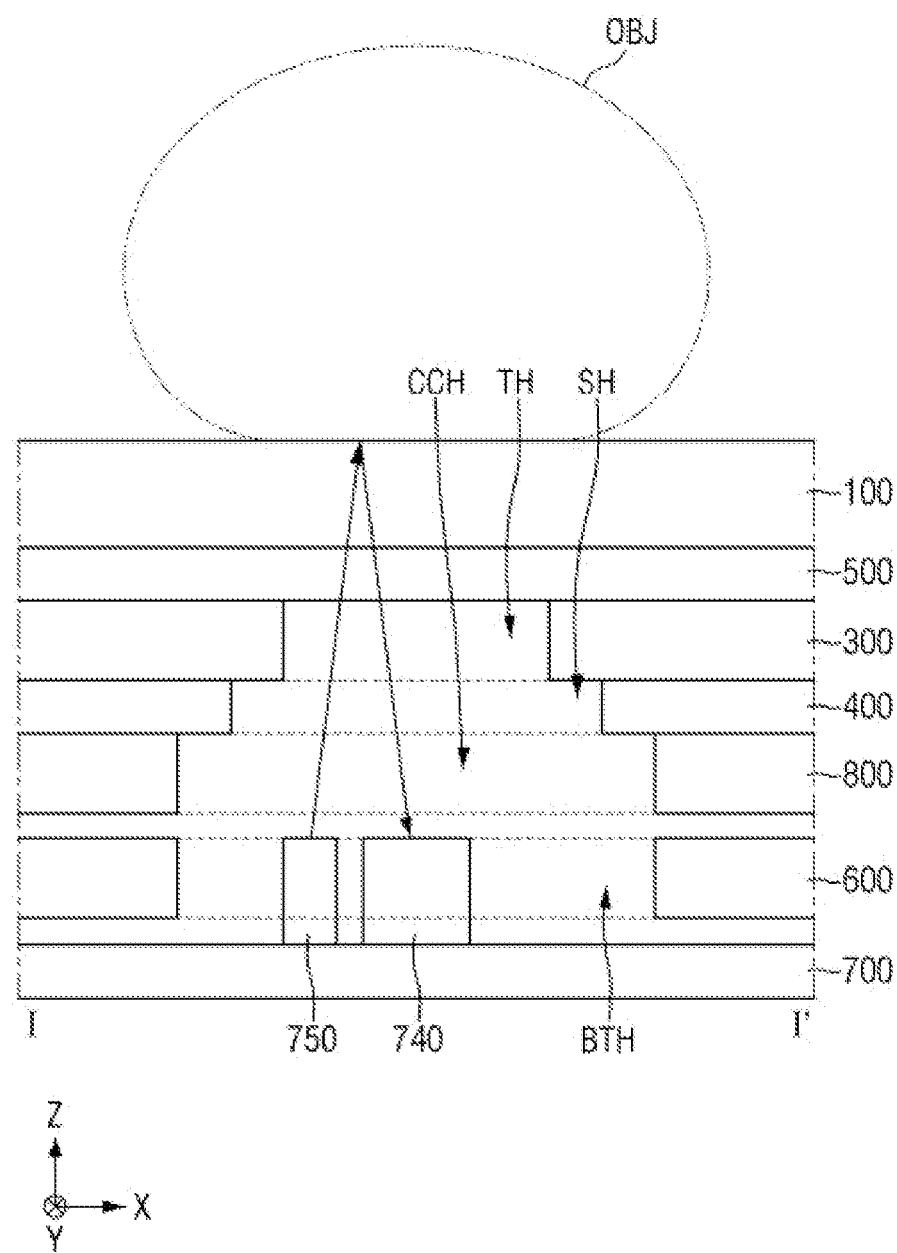
FIG. 6 is a cross-sectional view illustrating a cover window, a display panel, a force sensor, a bottom panel cover, a light emitting unit, and an optical sensor according to an exemplary embodiment of the invention.

In the blood pressure measurement mode, the display device 10 may measure the blood pressure of a user by using both the optical sensor 740 and the force sensor 400. As illustrated in FIG. 6, light output from a light emitting unit 750 may be reflected from the user's finger OBJ, and the light reflected from the user's finger OBJ may pass through the through hole TH to be sensed by the optical sensor 740. Regarding bodily functions, when a heart contracts, blood ejected from a left ventricle of the heart moves to peripheral tissues, which increases the arterial blood volume. Further, when the heart contracts, red blood cells carry more oxygen hemoglobin to the peripheral tissues. When the heart relaxes, the heart receives a partial influx of blood from the peripheral tissues. When light is irradiated to peripheral blood vessels, the irradiated light is absorbed by the peripheral tissues. Light absorbance depends on hematocrit and blood volume. The light absorbance may have a maximum value when the heart contracts and may have a minimum value when the heart relaxes. Therefore, light sensed by the optical sensor 740 may be a lowest amount when the heart contracts and may be a highest amount when the heart relaxes.

Further, when a user puts a finger on the display device 10 and lifts it off in the blood pressure measurement mode, a force (contact force) applied to the force sensor 400 may gradually increase to reach a maximum value, and then may gradually decrease. When the contact force increases, blood vessels may be narrowed, resulting in decreased or no blood flow. When the contact force decreases, the blood vessels expand, and blood may flow again. A further decrease of the contact force results in greater blood flow. Therefore, the change in the amount of light sensed by the optical sensor 740 may be proportional to the change in blood flow.

The main processor 710 may generate the pulse wave signal according to the force applied by the user, based on a force value calculated by the force sensor 400 and the optical signal according to the amount of light sensed by the optical sensor 740. Further, the main processor 710 may calculate the blood pressure based on the pulse wave signal. The pulse wave signal may have a waveform vibrating according to the cardiac cycle. For example, the main processor 710 may estimate the blood pressure of blood vessels of the user's finger OBJ based on time differences between time points corresponding to peaks of the generated pulse wave signal and time points corresponding to peaks of a filtered pulse wave signal. Among the estimated blood pressure values, a maximum blood pressure value may be determined as a systolic blood pressure value, and a minimum blood pressure value may be determined as a diastolic blood pressure value. Further, additional blood pressure values such as an average blood pressure value or the like may be calculated using the estimated blood pressure values. The calculated blood pressure value may be displayed on the display area DA of the display device 10 to be provided to the user.

The method of measuring the blood pressure described above is only exemplary, other various methods are disclosed in Korean Patent Application Publication No. 10-2018-0076050, Korean Patent Application Publication No. 10-2017-0049280, and Korean Patent Application Publication No. 10-2019-0040527, the disclosures of which are incorporated herein by reference in their entirety as fully disclosed herein.

Meanwhile, FIGS. 4 and 5 illustrate the user's finger OBJ as the user's body part where the blood pressure is measured, but the inventive concepts are not limited thereto. For example, the user's body part where the blood pressure is measured may be a wrist or other body parts.

FIG. 6 is a cross-sectional view illustrating a cover window, a display panel, a force sensor, a bottom panel cover, a light emitting unit, and an optical sensor according to an exemplary embodiment.

FIG. 6 illustrates an example of a cross section of the display device 10 taken along line I-I' of FIG. 4. FIG. 6 omits the lower cover 900 for convenience of illustration.

Referring to FIG. 6, the display device 10 may further include a polarization film 500, the light emitting unit 750, and a bottom panel cover 800.

The force sensor 400 may be disposed on one surface of the display panel 300. For example, the force sensor 400 may be disposed on the bottom surface of the display panel 300. In this case, the top surface of the force sensor 400 may be attached to the bottom surface of the display panel 300 via a transparent adhesive member.

The force sensor 400 may be disposed to overlap the display area DA of the display panel 300 in the third direction (Z-axis direction). For example, the force sensor 400 may completely overlap the display area DA of the display panel 300 in the third direction (Z-axis direction). Alternatively, a portion of the force sensor 400 may overlap the display area DA of the display panel 300 in the third direction (Z-axis direction), and the remaining portion may overlap the non-display area NDA of the display panel 300 in the third direction (Z-axis direction).

The force sensor 400 may include the sensor hole SH. The sensor hole SH may be a light transmitting portion capable of passing light. Alternatively, the sensor hole SH may be a physically formed hole (physical hole), such as a hole penetrating the force sensor 400. Alternatively, the sensor hole SH may have a shape in which the physical hole and the light transmitting portion are mixed.

The through hole TH of the display panel 300 may completely overlap the sensor hole SH of the force sensor 400. The size of the through hole TH of the display panel 300 may be smaller than the size of the sensor hole SH of the force sensor 400. The length of the through hole TH in one direction may be smaller than the length of the sensor hole SH in the one direction. For example, as illustrated in FIG. 6, the length of the through hole TH in the first direction (X-axis direction) may be smaller than the length of the sensor hole SH in the first direction (X-axis direction). Additionally, the height of the through hole TH in the second direction (Z-axis direction) may be higher than the height of the sensor hole in the second direction (Z-axis direction) Therefore, light passing through the through hole TH may be incident on the optical sensor 740 overlapping the through hole TH in the third direction (Z-axis direction) without being blocked by the force sensor 400.

The polarization film 500 may be disposed between the display panel 300 and the cover window 100. The polarization film 500 may include a first base member, a linear polarization plate, a quarter-wave plate (λ/4 plate), a half-wave plate (λ/2 plate), and a second base member. In this case, the first base member, the λ/4 plate, the λ/2 plate, the linear polarization plate, and the second base member may be sequentially stacked on the display panel 300.

The bottom panel cover 800 may be disposed on one surface of the force sensor 400. The bottom panel cover 800 may be attached to the bottom surface of the force sensor 400 via an adhesive member. The adhesive member may be a pressure sensitive adhesive (PSA). The bottom panel cover 800 may include at least one of a light blocking member (not illustrated) configured to absorb light incident from the outside, a buffer member (not illustrated) configured to absorb an impact from the outside, or a heat dissipation member (not illustrated) configured to efficiently dissipate heat from the display panel 300.

The light blocking member may be disposed under the force sensor 400. The light blocking member blocks light transmission, thereby preventing components (e.g., the display circuit board 310 and the like) disposed under the light blocking member from being viewed from the top of the display panel 300. The light blocking member may include a light absorbing material such as a black pigment, black dyes or the like. The light blocking member may be omitted.

The buffer member may be disposed under the light blocking member. The buffer member is configured to absorb an external impact to prevent the display panel 300 from being damaged. The buffer member may be formed of a single layer or multiple layers. For example, the buffer member may be formed of a polymer resin such as polyurethane (PU), polycarbonate (PC), polypropylene (PP), or polyethylene (PE) or may include an elastic material such as a foamed sponge obtained from rubber, a urethane-based material, or an acrylic material.

The heat dissipation member may be disposed under the buffer member. The heat dissipation member may include a first heat dissipation layer containing graphite, carbon nanotubes or the like, and a second heat dissipation layer formed of a metal thin film containing, for example, copper, nickel, ferrite, or silver which can shield electromagnetic waves and has excellent thermal conductivity.

The bottom panel cover 800 may include a cover hole CCH. The cover hole CCH may be the light transmitting portion capable of passing light. Alternatively, the cover hole CCH may be the physically formed hole (physical hole), such as a hole penetrating the bottom panel cover 800. Alternatively, the cover hole CCH may have a shape in which the physical hole and the light transmitting portion are mixed.

The through hole TH of the display panel 300 may completely overlap the cover hole CCH of the bottom panel cover 800. The size of the through hole TH of the display panel 300 may be smaller than the size of the cover hole CCH of the bottom panel cover 800. The length of the through hole TH in one direction may be smaller than the length of the cover hole CCH in the one direction. For example, as illustrated in FIG. 6, the length of the through hole TH in the first direction (X-axis direction) may be smaller than the length of the cover hole CCH in the first direction (X-axis direction). The height of the through hole TH in the second direction (Z-axis direction) may be substantially the same as the height of the sensor hole in the second direction (Z-axis direction).

Further, the sensor hole SH of the force sensor 400 may completely overlap the cover hole CCH of the bottom panel cover 800. The size of the sensor hole SH of the force sensor 400 may be smaller than the size of the cover hole CCH of the bottom panel cover 800. The length of the sensor hole SH in one direction may be smaller than the length of the cover hole CCH in the one direction. For example, as illustrated in FIG. 6, the length of the sensor hole SH in the first direction (X-axis direction) may be smaller than the length of the cover hole CCH in the first direction (X-axis direction).

The bracket 600 may be disposed on one surface of the force sensor 400. For example, the bracket 600 may be disposed on the lower surface of the force sensor 400. The bracket 600 may include the bracket hole BTH which is the physical hole penetrating the bracket 600. Alternatively, the bracket hole BTH may be the light transmitting portion capable of passing light. Alternatively, the bracket hole BTH may have a shape in which the physical hole and the light transmitting portion are mixed.

The through hole TH of the display panel 300 may completely overlap the bracket hole BTH of the bracket 600. The size of the through hole TH of the display panel 300 may be smaller than the size of the bracket hole BTH of the bracket 600. The length of the through hole TH in one direction may be smaller than the length of the bracket hole BTH in the one direction. For example, as illustrated in FIG. 6, the length of the through hole TH in the first direction (X-axis direction) may be smaller than the length of the bracket hole BTH in the first direction (X-axis direction).

Further, the sensor hole SH of the force sensor 400 may completely overlap the bracket hole BTH of the bracket 600.

The size of the sensor hole SH of the force sensor 400 may be smaller than the size of the bracket hole BTH of the bracket 600. The length of the sensor hole SH in one direction may be smaller than the length of the bracket hole BTH in the one direction. For example, as illustrated in FIG. 6, the length of the sensor hole SH in the first direction (X-axis direction) may be smaller than the length of the bracket hole BTH in the first direction (X-axis direction).

Further, the cover hole CCH of the bottom panel cover 800 may completely overlap the bracket hole BTH of the bracket 600. The size of the cover hole CCH of the bottom panel cover 800 may be substantially the same size of the bracket hole BTH of the bracket 600. The length of the cover hole CCH in one direction may be substantially the same length of the bracket hole BTH in the one direction. For example, as illustrated in FIG. 6, the length of the cover hole CCH in the first direction (X-axis direction) may be substantially the same length of the bracket hole BTH in the first direction (X-axis direction). Therefore, light may be incident on the optical sensor 740 after passing through the through hole TH, the sensor hole SH, the cover hole CCH, and the bracket hole BTH.

At least one of the optical sensor 740 or the light emitting unit 750 may be arranged in the bracket hole BTH of the bracket 600. Further, when the height of at least one of the optical sensor 740 or the light emitting unit 750 in the third direction (Z-axis direction) is relatively long, the at least one of the optical sensor 740 or the light emitting unit 750 may be also arranged in the cover hole CCH of the bottom panel cover 800. Alternatively, at least one of the optical sensor 740 or the light emitting unit 750 may be arranged in the sensor hole SH of the force sensor 400 and the cover hole CCH of the bottom panel cover 800. Alternatively, at least one of the optical sensor 740 or the light emitting unit 750 may be arranged in the through hole TH of the display panel 300, the sensor hole SH of the force sensor 400, and the cover hole CCH of the bottom panel cover 800. In this case, the through hole TH of the display panel 300, the sensor hole SH of the force sensor 400, and the cover hole CCH of the bottom panel cover 800 may all be the physical holes.

The light emitting unit 750 may include a light source that emits light. The light source may have, for example, at least one of a light emitting diode (LED), an organic light emitting diode (OLED), a laser diode (LD), quantum dots (QD), or a phosphor.

The wavelength of light emitted from the light emitting unit 750 may be an infrared wavelength, a visible wavelength, a wavelength of red light, or a wavelength of green light. Here, when the body part placed on the through hole TH is the finger OBJ whose blood vessels are fine, the wavelength of the light emitted from the light emitting unit 750 may be the infrared wavelength or the wavelength of red light. In this case, because the infrared wavelength or the wavelength of red light is longer than the wavelength of green light or a wavelength of blue light, it is easy for the light to enter the blood vessels of the finger to be absorbed. In addition, when the body part placed on the through hole TH is the wrist, the artery of the wrist is sufficiently thick. Therefore, even in the case where the wavelength of the light emitted from the light emitting unit 750 is the wavelength of green light, the green light may enter the artery of the wrist to be absorbed. In this manner, the wavelength of the light emitted from the light emitting unit 750 may be determined according to the body part subjected to blood pressure measurement.

The optical sensor 740 and the light emitting unit 750 may be disposed on one surface of the main processor 710. For example, the optical sensor 740 and the light emitting unit 750 may be mounted on the top surface of the main processor 710.

The optical sensor 740 and the light emitting unit 750 may overlap the through hole TH in the third direction (Z-axis direction). The optical sensor 740 and the light emitting unit 750 may be arranged in the bracket hole BTH of the bracket 600. Further, when the heights of the optical sensor 740 and the light emitting unit 750 are relatively long in the third direction (Z-axis direction), the optical sensor 740 and the light emitting unit 750 may be disposed in the sensor hole SH of the force sensor 400, or in both the through hole TH of the display panel 300 and the sensor hole SH of the force sensor 400. In this case, both the through hole TH of the display panel 300 and the sensor hole SH of the force sensor 400 may be the physical holes.

As illustrated in FIG. 6, the light emitted from the light emitting unit 750 may pass through the sensor hole SH of the force sensor 400 and the through hole TH of the display panel 300 to be absorbed by or reflected from the blood vessel of the user's finger OBJ. The light reflected from the blood vessel of the user's finger OBJ may pass through the through hole TH of the display panel 300 and the sensor hole SH of the force sensor 400 to be sensed by the optical sensor 740.

Meanwhile, FIG. 6 illustrates that the optical sensor 740 senses the light reflected from the finger OBJ after being emitted from the light emitting unit 750, but the inventive concepts are not limited thereto. For example, the optical sensor 740 may sense light reflected from the finger OBJ after being emitted from the display panel 300 instead of the light emitting unit 750. In this case, the light emitting unit 750 may be omitted.

Figure 7:
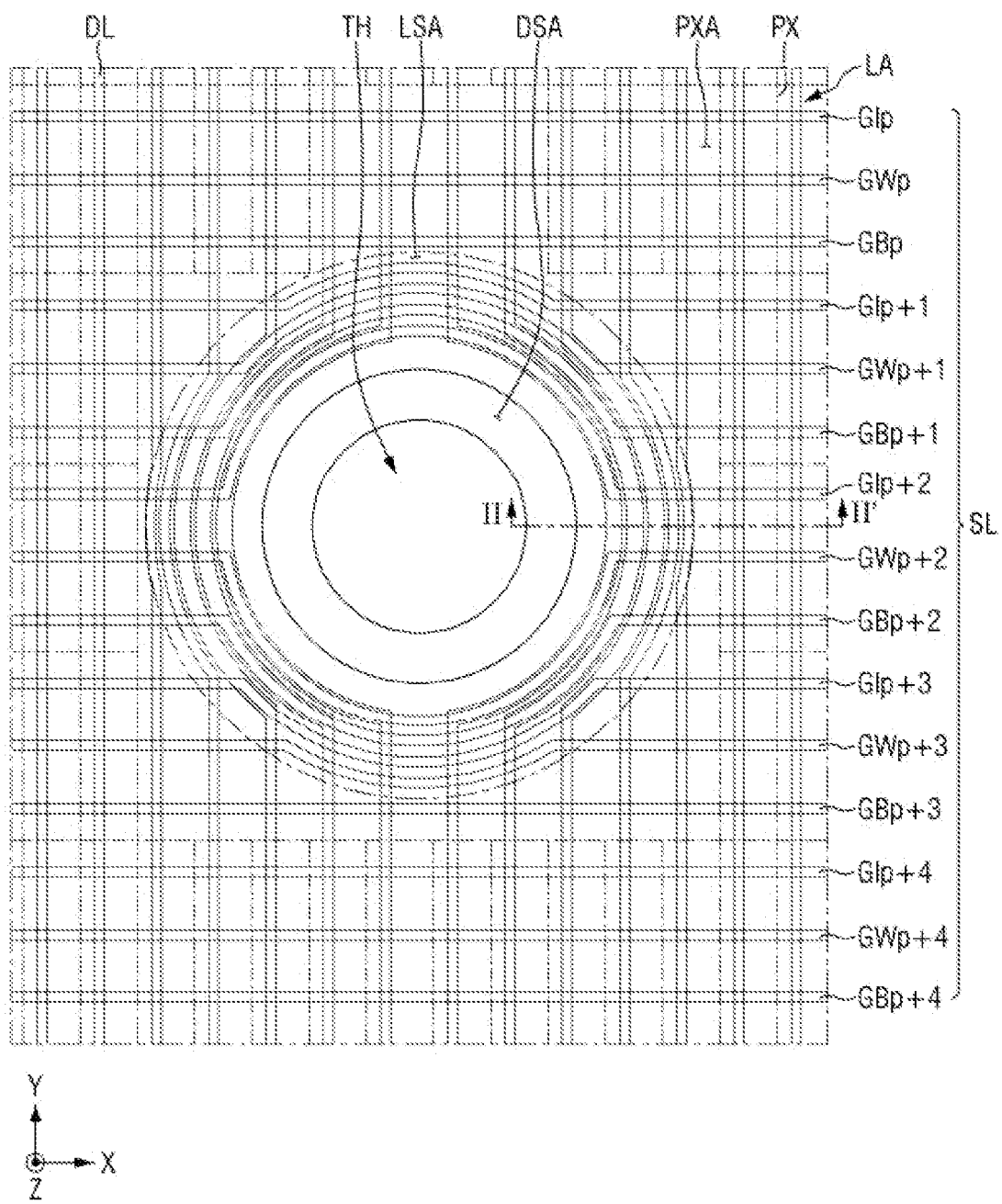
FIG. 7 is a layout diagram illustrating a display area and a through hole of a display panel according to an exemplary embodiment of the invention.

FIG. 7 is a layout diagram illustrating a display area and a through hole TH of a display panel according to an exemplary embodiment.

Referring to FIG. 7, the display area DA may include the through hole TH, a dead space area DSA, a wiring area LA, and a pixel area PXA.

The dead space area DSA may be arranged to surround the through hole TH. Pixels PX, scan lines SL, and data lines DL may not be disposed in the dead space area DSA. The dead space area DSA is an area configured to prevent the through hole TH from entering the wiring area LA due to a process error in the through hole TH forming process.

The wiring area LA (including the scan lines SL and data lines DL) may be disposed to surround the dead space area DSA. Because the pixels PX are not disposed in the wiring area LA, the wiring area LA corresponds to a non-display area that does not display an image.

The scan lines SL and the data lines DL that bypass the through hole TH may be disposed in the wiring area LA. The scan lines SL may include first initialization scan lines GIp to GIp+4, write scan lines GWp to GWp+4, and second initialization scan lines GBp to GBp+4.

The first initialization scan lines GIp to GIp+4, the write scan lines GWp to GWp+4, and the second initialization scan lines GBp to GBp+4 may extend in the first direction (X-axis direction). The first initialization scan lines GIp to GIp+4, the write scan lines GWp to GWp+4, and the second initialization scan lines GBp to GBp+4 may be curved in the second direction (Y-axis direction) to bypass the through hole TH. For example, among the first initialization scan lines GIp to GIp+4, the write scan lines GWp to GWp+4, and the second initialization scan lines GBp to GBp+4, scan lines that bypass the through hole TH to the upper side thereof may be curved in the upper direction. In contrast, among the first initialization scan lines GIp to GIp+4, the write scan lines GWp to GWp+4, and the second initialization scan lines GBp to GBp+4, scan lines that bypass the through hole TH to the lower side thereof may be curved in the lower direction. Alternatively, the first initialization scan lines GIp to GIp+4, the write scan lines GWp to GWp+4, and the second initialization scan lines GBp to GBp+4 may be bent in the form of a staircase to bypass the through hole TH.

The data lines DL may extend in the second direction (Y-axis direction) and curve towards a middle of the wiring area LA in the first direction (X-axis direction) to bypass the through hole TH. For example, among the data lines DL, lines that bypass the through hole TH to the left side thereof may be curved in the left direction. In contrast, among the data lines DL, lines that bypass the through hole TH to the right side thereof may be curved in the right direction. Alternatively, the data lines DL may be bent in the form of a staircase to bypass the through hole TH.

In order to minimize the size of the wiring area LA, a distance between the scan lines SL adjacent to each other in the wiring area LA may be smaller than that in the pixel area PXA. Further, a distance between the data lines DL adjacent to each other in the wiring area LA may be smaller than that in the pixel area PXA. Furthermore, in the wiring area LA, the scan lines may overlap the data lines DL in the third direction (Z-axis direction).

Each of the pixels PX may overlap any one of the first initialization scan lines GIp to GIp+4, any one of the write scan lines GWp to GWp+4, and any one of the second initialization scan lines GBp to GBp+4, and any one of the data lines DL.

As illustrated in FIG. 7, the scan lines and the data lines DL are designed to bypass the through hole TH in the wiring area LA, and the pixels PX are not arranged in the wiring area LA. Accordingly, even if the through hole TH is disposed to penetrate the display area DA of the display panel 300, the display panel 300 may stably display an image.

Figure 8:
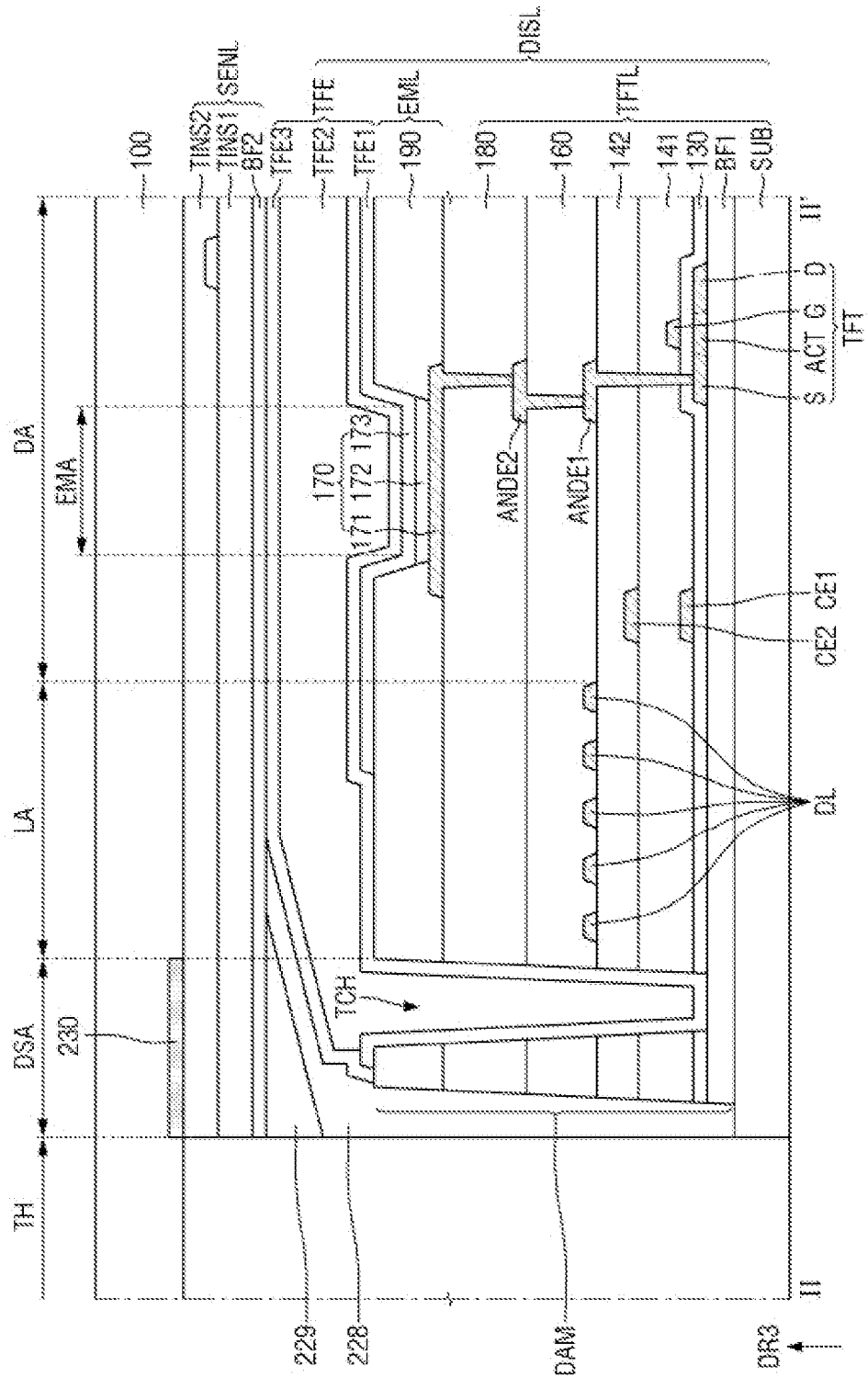
FIG. 8 is a cross-sectional view illustrating an example of the display panel of FIG. 7.

FIG. 8 is a cross-sectional view illustrating an example of the display panel of FIG. 7. FIG. 8 illustrates a cross section of the display panel 300 taken along line II-II' of FIG. 7.

Referring to FIG. 8, a first buffer film BF1, a thin film transistor layer TFTL, a light emitting element layer EML, an encapsulation layer TFE, and a touch electrode layer SENL may be sequentially disposed on the substrate SUB in that order.

The substrate SUB may be formed of an insulating material such as glass, quartz, or a polymer resin. For example, the substrate SUB may include polyimide. The substrate SUB may be a flexible substrate which can be bent, folded or rolled.

The first buffer film BF1 is a film configured to protect a thin film transistor TFT of the thin film transistor layer TFTL and a light emitting layer 172 of the light emitting element layer EML from moisture permeating through the substrate SUB which is susceptible to moisture permeation. The first buffer film BF1 may be formed of a plurality of inorganic layers that are alternately stacked. For example, the first buffer film BF1 may be formed of multiple layers in which one or more inorganic layers of a silicon nitride layer, a silicon oxynitride layer, a silicon oxide layer, a titanium oxide layer and an aluminum oxide layer are alternately stacked.

A light blocking layer may be disposed on the substrate SUB. The light blocking layer may be disposed to overlap an active layer ACT of the thin film transistor TFT to prevent a leakage current occurring when light is incident on the active layer ACT of the thin film transistor TFT. The light blocking layer may be covered by the first buffer film BF1. The light blocking layer may be formed as a single layer or multiple layers made of any one of molybdenum (Mo), aluminum (Al), chromium (Cr), gold (Au), titanium (Ti), nickel (Ni), neodymium (Nd) and copper (Cu) or an alloy thereof.

The thin film transistor layer TFTL includes the thin film transistor TFT, a gate insulating film 130, a first interlayer insulating film 141, a second interlayer insulating film 142, a first planarization film 160, and a second planarization film 180.

The active layer ACT, a source electrode S, and a drain electrode D may be formed on the first buffer film BF1. The active layer ACT may include polycrystalline silicon, monocrystalline silicon, low-temperature polycrystalline silicon, amorphous silicon, or an oxide semiconductor. When the active layer ACT is formed of polycrystalline silicon, the active layer ACT may have conductivity by ion doping. Therefore, the source electrode S and the drain electrode D may be formed by doping ions into active layers ACT.

The gate insulating film 130 may be formed on the active layer ACT, the source electrode S, and the drain electrode D. The gate insulating film 130 may be formed of an inorganic layer, for example, a silicon nitride layer, a silicon oxynitride layer, a silicon oxide layer, a titanium oxide layer, or an aluminum oxide layer.

A gate electrode G and a first capacitor electrode CE1 may be formed on the gate insulating film 130. The gate electrode G and the first capacitor electrode CE1 may be formed as a single layer or multiple layers made of any one of molybdenum (Mo), aluminum (Al), chromium (Cr), gold (Au), titanium (Ti), nickel (Ni), neodymium (Nd) and copper (Cu) or an alloy thereof.

The first interlayer insulating film 141 may be formed on the gate electrode G and the first capacitor electrode CE1. The first interlayer insulating film 141 may be formed of an inorganic layer, for example, a silicon nitride layer, a silicon oxynitride layer, a silicon oxide layer, a titanium oxide layer, or an aluminum oxide layer. The first interlayer insulating film 141 may include a plurality of inorganic layers.

A second capacitor electrode CE2 may be formed on the first interlayer insulating film 141. The second capacitor electrode CE2 may be formed as a single layer or multiple layers made of any one of molybdenum (Mo), aluminum (Al), chromium (Cr), gold (Au), titanium (Ti), nickel (Ni), neodymium (Nd) and copper (Cu) or an alloy thereof.

The second interlayer insulating film 142 may be formed on the second capacitor electrode CE2. The second interlayer insulating film 142 may be formed of an inorganic layer, for example, a silicon nitride layer, a silicon oxynitride layer, a silicon oxide layer, a titanium oxide layer, or an aluminum oxide layer. The second interlayer insulating film 142 may include a plurality of inorganic layers.

A first anode connection electrode ANDE1 may be formed on the second interlayer insulating film 142. The first anode connection electrode ANDE1 may be connected to the source electrode S through a contact hole penetrating the gate insulating film 130, the first interlayer insulating film 141, and the second interlayer insulating film 142. The first anode connection electrode ANDE1 may be formed as a single layer or multiple layers made of any one of molybdenum (Mo), aluminum (Al), chromium (Cr), gold (Au), titanium (Ti), nickel (Ni), neodymium (Nd) and copper (Cu) or an alloy thereof.

The first planarization film 160 may be formed on the first anode connection electrode ANDE1 to flatten steps formed due to the active layer ACT, the source electrode S, the drain electrode D, the gate electrode G, the first capacitor electrode CE1, the second capacitor electrode CE2 and the first anode connection electrode ANDE1. The first planarization film 160 may be formed of an organic layer such as acryl resin, epoxy resin, phenolic resin, polyamide resin, polyimide resin and the like.

A protective film 150 may be additionally formed between the first anode connection electrode ANDE1 and the first planarization film 160. The protective film 150 may be formed of an inorganic layer, for example, a silicon nitride layer, a silicon oxynitride layer, a silicon oxide layer, a titanium oxide layer, or an aluminum oxide layer.

A second anode connection electrode ANDE2 may be formed on the first planarization film 160. The second anode connection electrode ANDE2 may be connected to the first anode connection electrode ANDE1 through a contact hole penetrating the first planarization film 160. The second anode connection electrode ANDE2 may be formed as a single layer or multiple layers made of any one of molybdenum (Mo), aluminum (Al), chromium (Cr), gold (Au), titanium (Ti), nickel (Ni), neodymium (Nd) and copper (Cu) or an alloy thereof.

The second planarization film 180 may be formed on the second anode connection electrode ANDE2. The second planarization film 180 may be formed of an organic layer such as acryl resin, epoxy resin, phenolic resin, polyamide resin, polyimide resin and the like.

Although FIG. 8 illustrates that the thin film transistor TFT is formed by a top gate method in which the gate electrode G is located above the active layer ACT, the inventive concepts are not limited thereto. That is, the thin film transistor TFT may be formed by a bottom gate method in which the gate electrode G is located below the active layer ACT, or a double gate method in which the gate electrode G is located both above and below the active layer ACT.

The light emitting element layer EML is formed on the thin film transistor layer TFTL. The light emitting element layer EML includes light emitting elements 170 and a bank 190.

The light emitting elements 170 and the bank 190 are formed on the second planarization film 180. Each of the light emitting elements 170 may include a first light emitting electrode 171, the light emitting layer 172, and a second light emitting electrode 173.

The first light emitting electrode 171 may be formed on the second planarization film 180. The first light emitting electrode 171 may be connected to the second anode connection electrode ANDE2 through a contact hole penetrating the second planarization film 180.

In a top emission structure in which light is emitted toward the second light emitting electrode 173 when viewed with respect to the light emitting layer 172, the first light emitting electrode 171 may be formed of a metal material having high reflectivity to have a stacked structure (Ti/Al/Ti) of aluminum and titanium, a stacked structure (ITO/Al/ITO) of aluminum and ITO, an APC alloy, and a stacked structure (ITO/APC/ITO) of an APC alloy and ITO. The APC alloy is an alloy of silver (Ag), palladium (Pd) and copper (Cu).

The bank 190 may be formed on the second planarization film 180 to partition the first light emitting electrode 171, thereby defining a light emitting area EMA. The bank 190 may be formed to cover the edge of the first light emitting electrode 171. The bank 190 may be formed of an organic layer such as acryl resin, epoxy resin, phenolic resin, polyamide resin, polyimide resin and the like.

The light emitting area EMA represents an area in which the first emitting electrode 171, the light emitting layer 172, and the second emitting electrode 173 are sequentially stacked, and holes from the first emitting electrode 171 and electrons from the second emitting electrode 173 are combined each other to emit light in the light emitting layer 172.

The light emitting layer 172 is formed on the first light emitting electrode 171 and the bank 190. The light emitting layer 172 may include an organic material to emit light in a predetermined color. For example, the light emitting layer 172 may include a hole transporting layer, an organic material layer, and an electron transporting layer.

The second light emitting electrode 173 is formed on the light emitting layer 172. The second light emitting electrode 173 may be formed to cover the light emitting layer 172. The second light emitting electrode 173 may be a common layer which is commonly formed in sub-pixels SP1, SP2, and SP3. A capping layer may be formed on the second light emitting electrode 173.

In the top emission type structure, the second light emitting electrode 173 may be formed of a transparent conductive material (TCO) such as ITO or IZO capable of transmitting light or a semi-transmissive conductive material such as magnesium (Mg), silver (Ag), or an alloy of magnesium (Mg) and silver (Ag). When the second light emitting electrode 173 is formed of a semi-transmissive metal material, the light emission efficiency can be increased due to a micro-cavity effect.

The encapsulation layer TFE may be formed on the light emitting element layer EML. The encapsulation layer TFE may include at least one inorganic layer to prevent oxygen or moisture from penetrating into the light emitting element layer EML. In addition, the encapsulation layer TFE may include at least one organic layer to protect the light emitting element layer EML from foreign substances such as dust. For example, the encapsulation layer TFE may include a first inorganic film TFE1, an organic film TFE2, and a second inorganic film TFE3.

The first inorganic film TFE1, the organic film TFE2 and the second inorganic film TFE3 may be sequentially disposed on the second light emitting electrode 173 in that order. The first inorganic film TFE1 and the second inorganic film TFE3 may be formed of multiple layers in which one or more inorganic layers of a silicon nitride layer, a silicon oxynitride layer, a silicon oxide layer, a titanium oxide layer and an aluminum oxide layer are alternately stacked. The organic film TFE2 may be a monomer.

The touch electrode layer SENL is disposed on the encapsulation layer TFE. The touch electrode layer SENL includes a second buffer film BF2, touch electrodes SE, and a first touch insulating film TINS1.

The second buffer film BF2 may be disposed on the encapsulation layer TFE. The second buffer film BF2 may include at least one inorganic layer. For example, the second buffer film BF2 may be formed of multiple layers in which one or more inorganic layers of a silicon nitride layer, a silicon oxynitride layer, a silicon oxide layer, a titanium oxide layer and an aluminum oxide layer are alternately stacked. The second buffer film BF2 may be omitted.

The first touch insulating film TINS1 may be disposed on the second buffer film BF2. The first touch insulating film TINS1 may be formed of an inorganic layer, for example, a silicon nitride layer, a silicon oxynitride layer, a silicon oxide layer, a titanium oxide layer, or an aluminum oxide layer. Alternatively, the first touch insulating film TINS1 may be formed of an organic layer such as acryl resin, epoxy resin, phenolic resin, polyamide resin, polyimide resin and the like.

The touch electrodes SE may be disposed on the first touch insulating film TINS1. The touch electrodes SE do not overlap the light emitting area EMA. That is, the touch electrodes SE are not disposed in the light emitting area EMA. The touch electrodes SE may be formed of a single layer containing molybdenum (Mo), titanium (Ti), copper (Cu), or aluminum (Al), or may be formed to have a stacked structure (Ti/Al/Ti) of aluminum and titanium, a stacked structure (ITO/Al/ITO) of aluminum and indium tin oxide (ITO), an Ag—Pd—Cu (APC) alloy, or a stacked structure (ITO/APC/ITO) of APC alloy and ITO.

A second touch insulating film TINS2 may be disposed on the touch electrodes SE. The second touch insulating film TINS2 may include at least one of an inorganic layer or an organic layer. The inorganic layer may be a silicon nitride layer, a silicon oxynitride layer and a silicon oxide layer, a titanium oxide layer, or an aluminum oxide layer. The organic layer may include acryl resin, epoxy resin, phenolic resin, polyamide resin, or polyimide resin.

The polarization film 500 may be disposed on the touch electrode layer SENL, and the cover window 100 may be disposed on the polarization film 500. An impact absorbing layer may be additionally disposed between the polarization film 500 and the cover window 100.

A dam structure DAM may be disposed around the through hole TH. The dam structure DAM may include at least one of the insulating film BF1, 130, 141, 142, 160, 180, or 190 stacked in the thin film transistor layer TFTL and the light emitting element layer EML. A trench TCH from which the insulating films BF1, 130, 141, 142, 160, 180, and 190 are removed may be disposed between the dam structure DAM and the light emitting area EMA. At least a portion of the encapsulation layer TFE may be disposed in the trench TCH. For example, the organic film TFE2 of the encapsulation layer TFE may be disposed up to the dam structure DAM, and may not be disposed between the dam structure DAM and the through hole TH. That is, it is possible to prevent the organic film TFE2 from overflowing into the through hole TH by the dam structure DAM. FIG. 8 illustrates that the first inorganic film TFE1 and the second inorganic film TFE3 end on the dam structure DAM, but the inventive concepts are not limited thereto. For example, the first inorganic film TFE1 and the second inorganic film TFE3 may end in an area between the dam structure DAM and the through hole TH.

A light blocking pattern 230 may be disposed on one surface of the cover window 100. The light blocking pattern 230 may overlap the dam structure DAM in the third direction (Z-axis direction). The light blocking pattern 230 may overlap the edge of the through hole TH in the third direction (Z-axis direction).

At least one of an organic film 228 or 229 may be further disposed on the encapsulation layer TFE in the area between the dam structure DAM and the through hole TH. For example, the first organic film 228 may be disposed on the second inorganic film TFE3, and the second organic film 229 may be disposed on the first organic film 228. The first organic film 228 and the second organic film 229 may serve to fill the space between the dam structure DAM and the through hole TH to perform the planarization.

Figure 9:
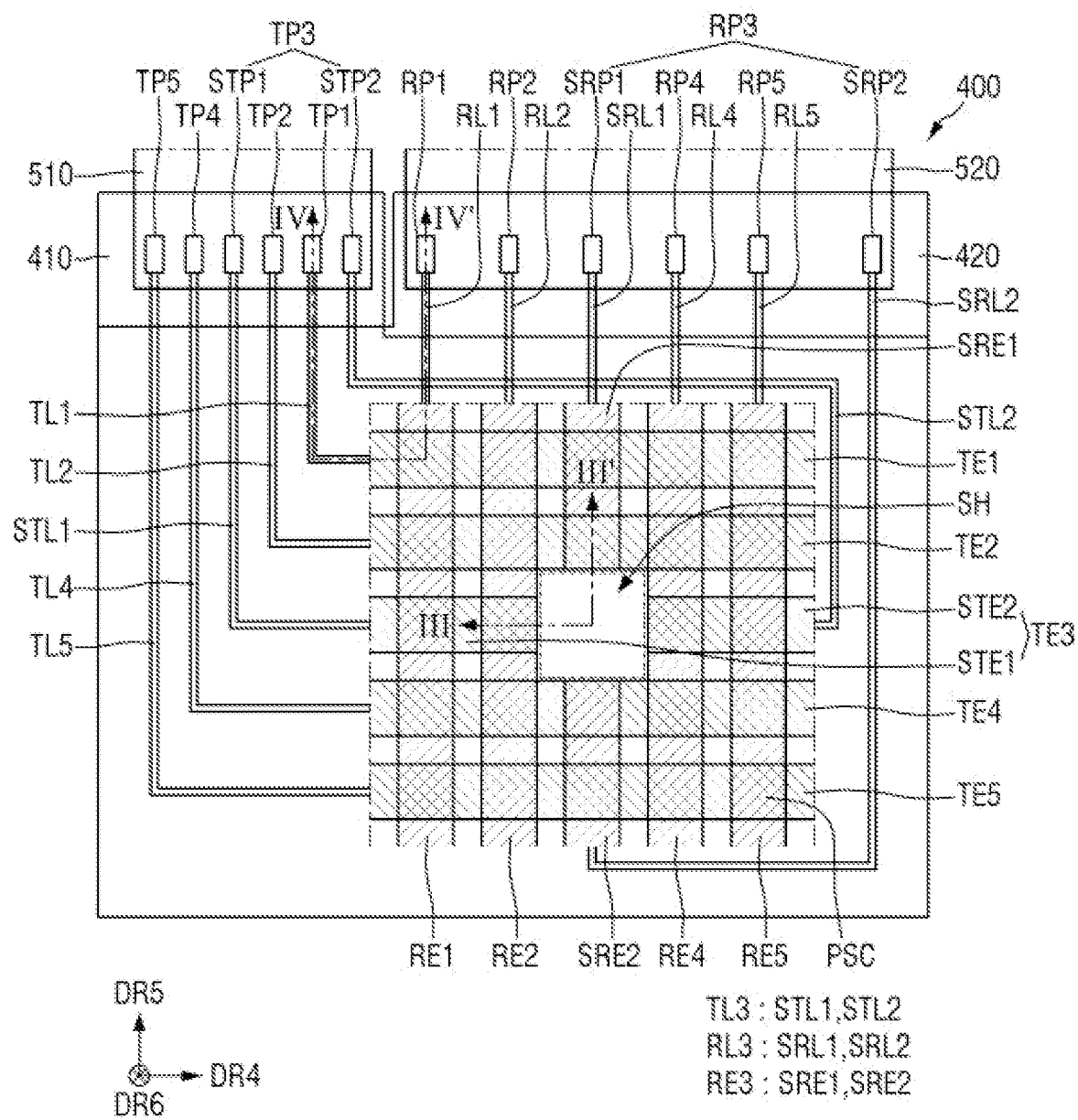
FIG. 9 is a layout view illustrating force sensor electrodes and a sensor hole of a force sensor according to an exemplary embodiment of the invention.
Figure 10:
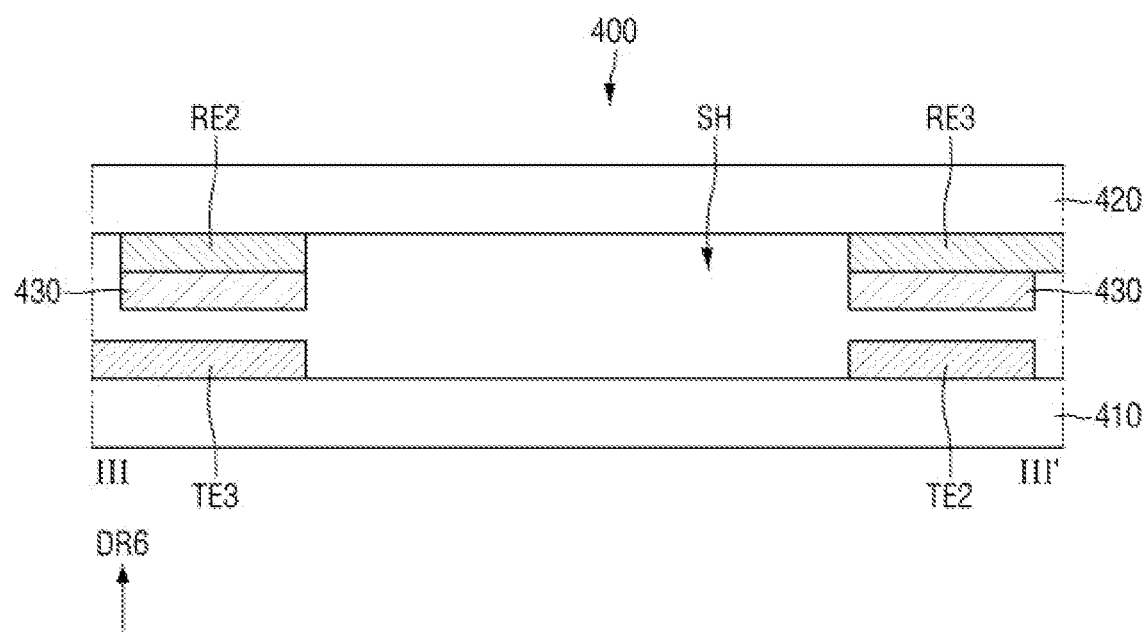
FIGS. 10 and 11 are cross-sectional views illustrating an example of the force sensor of FIG. 9.
Figure 11:
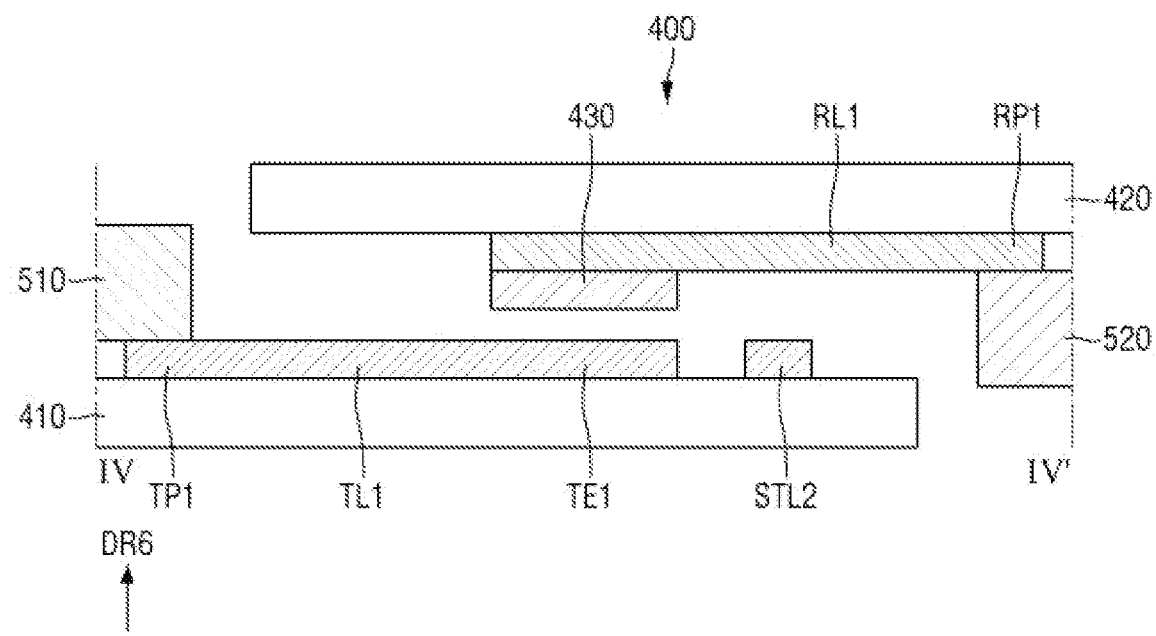

FIG. 9 is a layout view illustrating force sensor electrodes and a sensor hole of a force sensor according to an exemplary embodiment. FIGS. 10 and 11 are cross-sectional views illustrating an example of the force sensor of FIG. 9.

FIG. 10 illustrates an example of a cross section of the force sensor taken along line III-III' of FIG. 9, and FIG. 11 illustrates an example of a cross section of the force sensor taken along line IV-IV' of FIG. 9.

Referring to FIGS. 9 to 11, the force sensor 400 may include a first base substrate 410, first force sensor electrodes, first force sensor wirings, first force pads, a second base substrate 420, second force sensor electrodes, second force sensor wirings, second force pads, force sensitive layers 430, force sensing cells PSC, and the sensor hole SH.

Each of the first base substrate 410 and the second base substrate 420 may include a polyethylene, polyimide, polycarbonate, polysulfone, polyacrylate, polystyrene, polyvinyl chloride, polyvinyl alcohol, polynorbornene, or polyester-based material. In one embodiment, each of the first base substrate 410 and the second base substrate 420 may be made of a polyethylene terephthalate (PET) film or a polyimide film.

The first base substrate 410 and the second base substrate 420 may be bonded to each other via a bonding layer. The bonding layer may include an adhesive material. The bonding layer may be disposed along the edges of the first base substrate 410 and the second base substrate 420, but the inventive concepts are not limited thereto.

In FIGS. 9 to 11, the first force sensor electrodes correspond to force driving electrodes TE1 to TE5 to which driving signals are applied, and the second force sensor electrodes correspond to force sensing electrodes RE1 to RE5 which provide sensing signals, for convenience of illustration. Further, in FIGS. 9 to 11, the first force sensor wirings correspond to force driving wirings TL1 to TL5, the second force sensor wirings correspond to force sensing wirings RL1 to RL5, the first force pads correspond to force driving pads TP1 to TP5, and the second force pads correspond to force sensing pads RP1 to RP5, for convenience of illustration. Furthermore, FIGS. 9 to 11 illustrate that the force sensor 400 includes five force driving electrodes TE1 to TE5 and five force sensing electrodes RE1 to RE5, but the number of the force driving electrodes TE1 to TE5 and the number of force sensing electrodes RE1 to RE5 are not limited thereto.

The force driving electrodes TE1 to TE5 may be disposed on one surface of the first base substrate 410 facing the second base substrate 420. The force sensing electrodes RE1 to RE5 may be disposed on one surface of the second base substrate 420 facing the first base substrate 410. The force driving electrodes TE1 to TE5 and the force sensing electrodes RE1 to RE5 may include conductive materials. For example, the force driving electrodes TE1 to TE5 and the force sensing electrodes RE1 to RE5 may be formed of metal such as silver (Ag) and copper (Cu), transparent conductive oxide such as indium tin oxide (ITO), indium zinc oxide (IZO) or zinc tin oxide (ZTO), carbon nanotubes, a conductive polymer, or the like.

The force driving electrodes TE1 to TE5 may extend in a fourth direction DR4 and may be arrayed in a fifth direction DR5. The force sensing electrodes RE1 to RE5 may extend in the fifth direction DR5 and may be arrayed in the fourth direction DR4. The force driving electrodes TE1 to TE5 and the force sensing electrodes RE1 to RE5 may cross each other. Crossing regions of the force driving electrodes TE1 to TE5 and the force sensing electrodes RE1 to RE5 may be arrayed in a matrix form.

The force sensitive layers 430 may be respectively disposed in the crossing regions of the force driving electrodes TE1 to TE5 and the force sensing electrodes RE1 to RE5. The force sensitive layers 430 may be respectively disposed between the force driving electrodes TE1 to TE5 and the force sensing electrodes RE1 to RE5. That is, the force sensitive layer 430 may be disposed between any one of the force driving electrodes TE1 to TE5 and any one of the force sensing electrodes RE1 to RE5. The force sensitive layer 430 may contact at least one of the force driving electrode or the force sensing electrode. For example, the force sensitive layer 430 may contact the force sensing electrode as illustrated in FIG. 10.

The force sensitive layer 430 may include a force sensitive material. The force sensitive material may contain metal nanoparticles formed of, for example, nickel, aluminum, tin, copper and the like, or carbon. The force sensitive material may be provided in polymer resin in the form of particles, but the inventive concepts are not limited thereto.

When a force is applied to the force sensor 400, the force sensitive layer 430 may also contact the one or more force driving electrodes TE. Consequently, the at least one force driving electrodes TE, the force sensitive layer 430, and at least one of the force sensing electrodes may be electrically connected to each other. As the force applied to the force sensor 400 becomes greater, electrical resistance of the force sensitive layer 430 may become lower.

By applying driving voltages to the force driving electrodes TE to TE5 and measuring sensed voltages by the force sensing electrodes RE1 to RE5, it is possible to calculate the electrical resistance of each of the force sensitive layers 430 disposed in the crossing regions of the force driving electrodes TE1 to TE5 and the force sensing electrodes RE1 to RE5. A force value that corresponds to the magnitude of the force may be calculated according to the electrical resistance of each of the force sensitive layers 430. In order to calculate the force value, the crossing regions of the force driving electrodes TE1 to TE5 and the force sensing electrodes RE1 to RE5, in which the force sensitive layers 430 are disposed, may be defined as force sensing cells PCE, respectively.

The force driving wirings TL1 to TL5 and the force driving pads TP1 to TP5 may be disposed on the one surface of the first base substrate 410. The force driving wirings TL1 to TL5 and the force driving pads TP1 to TP5 may include a conductive material. For example, the force driving wirings TL1 to TL5 and the force driving pads TP1 to TP5 may be formed of metal such as silver (Ag) or copper (Cu), transparent conductive oxide such as ITO, IZO or ZTO, carbon nanotubes, a conductive polymer or the like.

The force driving wirings TL1 to TL5 may connect the force driving electrodes TE1 to TE5 to the force driving pads TP1 to TP5, respectively. For example, the first force driving wiring TL1 may connect the first force driving electrode TE1 to the first force driving pad TP1, and the second force driving wiring TL2 may connect the second force driving electrode TE2 to the second force driving pad TP2. The third force driving wiring TL3 may connect the third force driving electrode TE3 to the third force driving pad TP3, the fourth force driving wiring TL4 may connect the fourth force driving electrode TE4 to the fourth force driving pad TP4, and the fifth force driving wiring TL5 may connect the fifth force driving electrode TE5 to the fifth force driving pad TP5.

The force driving pads TP1 to TP5 may be disposed at one side of the first base substrate 410. A force driving circuit board 510 may be disposed on the force driving pads TP1 to TP5. The force driving circuit board 510 may be attached to the force driving pads TP1 to TP5 using an anisotropic conductive film or the like. Accordingly, the force driving pads TP1 to TP5 may be electrically connected to the force driving circuit board 510. In addition, because the force driving circuit board 510 is electrically connected to the display circuit board 310, the force sensor 400 may be electrically connected to the force driving circuit 340 of the display circuit board 310.

The force sensing wirings RL1 to RL5 and the force sensing pads RP1 to RP5 may be disposed on one surface of the second base substrate 420. The force sensing wirings RL1 to RL5 and the force sensing pads RP1 to RP5 may include a conductive material. For example, the force sensing wirings RL1 to RL5 and the force sensing pads RP1 to RP5 may be formed of metal such as silver (Ag) or copper (Cu), transparent conductive oxide such as ITO, IZO or ZTO, carbon nanotubes, a conductive polymer or the like.

The force sensing wirings RL1 to RL5 may connect the force sensing electrodes RE1 to RE5 to the force sensing pads RP1 to RP5, respectively. For example, the first force sensing wiring RL1 may connect the first force sensing electrode RE1 to the first force sensing pad RP1, and the second force sensing wiring RL2 may connect the second force sensing electrode RE2 to the second force sensing pad RP2. The third force sensing wiring RL3 may connect the third force sensing electrode RE3 to the third force sensing pad RP3, the fourth force sensing wiring RL4 may connect the fourth force sensing electrode RE4 to the fourth force sensing pad RP4, and the fifth force sensing wiring RL5 may connect the fifth force sensing electrode RE5 to the fifth force sensing pad RP5.

The force sensing pads RP1 to RP5 may be disposed at one side of the second base substrate 420. A force sensing circuit board 520 may be disposed on the force sensing pads RP1 to RP5. The force sensing circuit board 520 may be attached to the force sensing pads RP1 to RP5 using an anisotropic conductive film or the like. Accordingly, the force sensing pads RP1 to RP5 may be electrically connected to the force sensing circuit board 520. In addition, because the force sensing circuit board 520 is electrically connected to the display circuit board 310, the force sensor 400 may be electrically connected to the force driving circuit 340 of the display circuit board 310.

Meanwhile, as illustrated in FIGS. 9 and 11, the force driving circuit board 510 may be attached to one surface of the first base substrate 410, and the force sensing circuit board 520 may be attached to one surface of the second base substrate 420. In order to prevent the force driving circuit board 510 from being interfered by the second base substrate 420, the second base substrate 420 may not be disposed above the one surface of the first base substrate 410 to which the force driving circuit board 510 is attached. In addition, in order to prevent the force sensing circuit board 520 from being interfered by the first base substrate 410, the first base substrate 410 may not be disposed above the one surface of the second base substrate 420 to which the force sensing circuit board 520 is attached.

The force driving pads TP1 to TP5 and the force sensing pads RP1 to RP5 may not overlap each other in a sixth direction DR6, which is the thickness direction of the force sensor 400. For example, as illustrated in FIG. 9, the force driving pads TP1 to TP5 may be disposed at the upper left side of the first base substrate 410, and the force sensing pads RP1 to RP5 may be disposed at the upper right side of the second base substrate 420. In addition, the upper left side of the first base substrate 410 may protrude in the fifth direction DR5 compared to the upper right side thereof, and the upper right side of the second base substrate 420 may protrude in the fifth direction DR5 compared to the upper left side thereof.

When the force driving electrodes TE1 to TE5 and the force sensing electrodes RE1 to RE5 include an opaque conductive material or the force sensitive layers 430 include opaque polymer resin, the force sensor 400 may have considerably low light transmittance. The force sensor 400 may include the sensor hole SH to prevent light passing through the through hole TH of the display panel 300 from being blocked by the force sensor 400.

The sensor hole SH may be disposed in the crossing region of any one of the force driving electrodes TE1 to TE5 and any one of the force sensing electrodes RE1 to RE5, as the light transmitting portion that allows light to pass therethrough. For example, as illustrated in FIG. 9, the sensor hole SH may be disposed in the crossing region of the third force driving electrode TE3 and the third force sensing electrode RE3. In this case, a component including an opaque material may be removed from the third force driving electrode TE3, the third force sensing electrode RE3, and the force sensitive layer 430 disposed in the crossing region of the third force driving electrode TE3 and the third force sensing electrode RE3. For example, when the third force driving electrode TE3 and the third force sensing electrode RE3 include the opaque conductive material, the third force driving electrode TE3 and the third force sensing electrode RE3 may be removed from the sensor hole SH as illustrating in FIG. 10. When the force sensitive layer 430 includes the opaque polymer resin, the force sensitive layer 430, which is disposed in the crossing region of the third force driving electrode TE3 and the third force sensing electrode RE3, may be removed from the sensor hole SH as illustrated in FIG. 10.

The third force driving electrode TE3 may include a first sub-force sensor electrode STE1 and a second sub-force sensor electrode STE2 which are divided by the sensor hole SH. The first sub-force driving electrode STE1 may be disposed on a first side (for example, the left side in FIG. 9) of the sensor hole SH, and the second sub-force driving electrode STE2 may be disposed on a second side (for example, the right side in FIG. 9) of the sensor hole SH.

Because the third force driving electrode TE3 is divided into the first sub-force driving electrode STE1 and the second sub-force driving electrode STE2 by the sensor hole SH, the length of the first sub-force driving electrode STE1 in the fourth direction DR4 and the length of the second sub-force driving electrode STE2 in the fourth direction DR4 may be smaller than the length of each of the force driving electrodes TE1, TE2, TE4 and TE5 in the fourth direction DR4 except for the third force driving electrode TE3 among the force driving electrodes TE1 to TE5.

Because the first sub-force driving electrode STE1 and the second sub-force driving electrode STE2 are separated by the sensor hole SH, the first sub-force driving electrode STE1 and the second sub-force driving electrode STE2 may be connected to a first sub-force sensor wiring and a second sub-force sensor wiring, respectively. The first sub-force sensor wiring may be a first sub-force driving wiring STL1, and the second sub-force sensor wiring may be a second sub-force driving wiring STL2. The third force driving wiring TL3 may include the first sub-force driving wiring STL1 connected to the first sub-force driving electrode STE1 and the second sub-force driving wiring STL2 connected to the second sub-force driving electrode STE2.

The first sub-force driving wiring STL1 may connect the first sub-force driving electrode STE1 to a first sub-force sensor pad STP1 of the third force driving pad TP3. The second sub-force driving wiring STL2 may connect the second sub-force driving electrode STE2 to a second sub-force sensor pad STP2 of the third force driving pad TP3.

The first force driving electrode TE1, the second force driving electrode TE2, the fourth force driving electrode TE4, the fifth force driving electrode TE5, and the first sub-force driving electrode STE1 may be connected, at first side ends (for example, the left ends in FIG. 9) thereof, to the first force driving wiring TL1, the second force driving wiring TL2, the fourth force driving wiring TL4, the fifth force driving wiring TL5, and the first sub-force driving wiring STL1, respectively. In contrast, the second sub-force driving electrode STE2 may be connected to the second sub-force driving wiring STL2 at a second side end (for example, the right end in FIG. 9) thereof. Because the second sub-force driving wiring STL2 is connected to the second sub-force driving pad STP2 after passing through the right portion and upper portion of the force sensor 400, the second sub-force driving wiring STL2 may cross the first and second force sensing wirings RL1 and RL2, the fourth and fifth force sensing wirings RL4 and RL5, and the first sub-force sensing wiring SRL1 at the upper portion of the force sensor 400.

The third force sensing electrode RE3 may include a third sub-force sensor electrode SRE1 and a fourth sub-force sensor electrode SRE2 divided by the sensor hole SH. The first sub-force sensing electrode SRE1 may be disposed on a third side (for example, the upper side in FIG. 9) of the sensor hole SH, and the second sub-force sensing electrode SRE2 may be disposed on a fourth side (for example, the lower side in FIG. 9) of the sensor hole SH.

Because the third force sensing electrode RE3 is divided into the first sub-force sensing electrode SRE1 and the second sub-force sensing electrode SRE2 by the sensor hole SH, the length of the first sub-force sensing electrode SRE1 in the fifth direction DR5 and the length of the second sub-force sensing electrode SRE2 in the fifth direction DR5 may be smaller than the length of each of the force sensing electrodes RE1, RE2, RE4, and RE5 in the fifth direction DR5 except for the third force sensing electrode RE3 among the force sensing electrodes RE1 to RE5.

Because the first sub-force sensing electrode SRE1 and the second sub-force sensing electrode SRE2 are disconnected by the sensor hole SH, the first sub-force sensing electrode SRE1 and the second sub-force sensing electrode SRE2 may be connected to a third sub-force sensor wiring and a fourth sub-force sensor wiring, respectively. The third sub-force sensor wiring may be a first sub-force sensing wiring SRL1, and the second sub-force sensor wiring may be a second sub-force sensing wiring SRL2. The third force sensing wiring RL3 may include the first sub-force sensing wiring SRL1 connected to the first sub-force sensing electrode SRE1 and the second sub-force sensing wiring SRL2 connected to the second sub-force sensing electrode SRE2.

The first sub-force sensing wiring SRL1 may connect the first sub-force sensing electrode SRE1 to a third sub-force sensor pad of the third force sensing pad RP3. The second sub-force sensing wiring SRL2 may connect the second sub-force sensing electrode SRE2 to a fourth sub-force sensor pad of the third force sensing pad RP3. The third sub-force sensor pad may be a first sub-force sensing pad SRP1, and the fourth sub-force sensor pad may be a second sub-force sensing pad SRP2.

The first force sensing electrode RE1, the second force sensing electrode RE2, the fourth force sensing electrode RE4, the fifth force sensing electrode RE5, and the first sub-force sensing electrode SRE1 may be connected, at third side ends (for example, the upper ends in FIG. 9) thereof, to the first force sensing wiring RL1, the second force sensing wiring RL2, the fourth force sensing wiring RL4, the fifth force sensing wiring RL5 and the first sub-force sensing wiring SRL1, respectively. In contrast, the second sub-force sensing electrode SRE2 may be connected to the second sub-force sensing wiring SRL2 at a fourth side end (for example, the lower end in FIG. 9) thereof. The second sub-force sensing wiring SRL2 may be connected to a second sub-force sensing pad SRP2 after passing through the lower portion and right portion of the force sensor 400.

The lengths of the force sensor 400 in the fourth direction DR4 and in the fifth direction DR5 may be in a range of about 10 mm to 20 mm, but the inventive concepts are not limited thereto. The lengths of each force sensing cell PSC in the fourth direction DR4 and in the fifth direction DR5 may be about 1.5 mm or more. The lengths of the sensor hole SH in the fourth direction DR4 and in the fifth direction DR5 may be about 3 mm or more.

As illustrated in FIGS. 9 to 11, although the first sub-force driving electrode STE1 and the second sub-force driving electrode STE2 are disconnected by the sensor hole SH, the first and second sub-force driving electrodes STE1 and STE2 are respectively connected to the sub-force driving wirings STL1 and STL2, so that the first and second sub-force driving electrodes STE1 and STE2 can be electrically connected to the force driving circuit 340. In addition, although the first sub-force sensing electrode SRE1 and the second sub-force sensing electrode SRE2 are disconnected by the sensor hole SH, the first and second sub-force sensing electrodes SRE1 and SRE2 are respectively connected to the sub-force sensing wirings SRL1 and SRL2, so that the first and second sub-force sensing electrodes SRE1 and SRE2 can be electrically connected to the force driving circuit 340.

Figure 12:
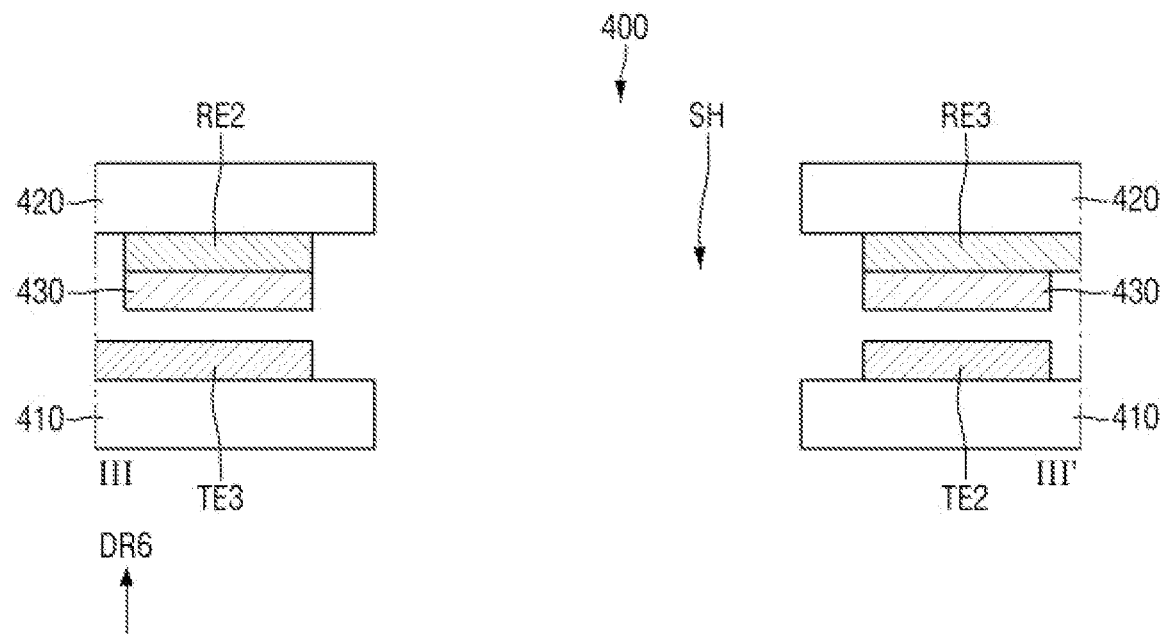
FIG. 12 is a cross-sectional view illustrating another example of the force sensor of FIG. 9.

FIG. 12 is a cross-sectional view illustrating another example of the force sensor of FIG. 9. FIG. 12 illustrated another example of a cross section of the force sensor taken along line III-III' of FIG. 9.

The embodiment of FIG. 12 is different from the embodiment of FIG. 10 in that the sensor hole SH is a physical hole which is physically formed. Therefore, a description overlapping with the embodiment of FIG. 10 is omitted to avoid redundancy.

Referring to FIG. 12, in the case where the sensor hole SH is disposed in the crossing region of the third force driving electrode TE3 and the third force sensing electrode RE3, the sensor hole SH may be the physical hole from which not only the third force driving electrode TE3, the third force sensing electrode RE3, and the force sensitive layer 430 disposed in the crossing region of the third force driving electrode TE3 and the third force sensing electrode RE3 but also the first base substrate 410 and the second base substrate 420 have been removed. In this case, the optical sensor 740 may be arranged in the sensor hole SH.

Figure 13:
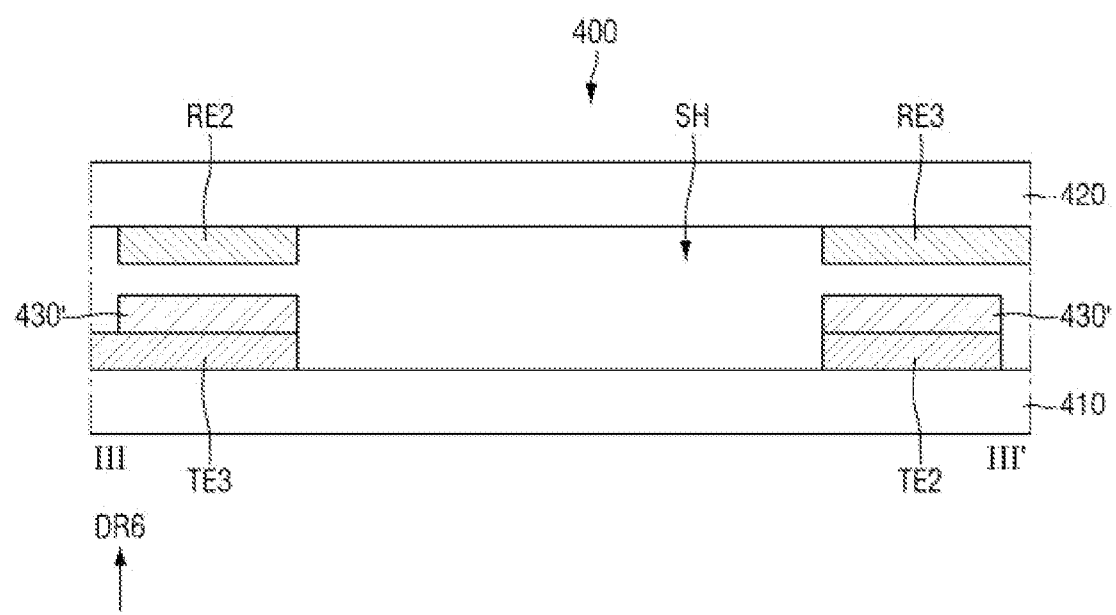
FIGS. 13 and 14 are cross-sectional views illustrating still another example of the force sensor of FIG. 9.
Figure 14:
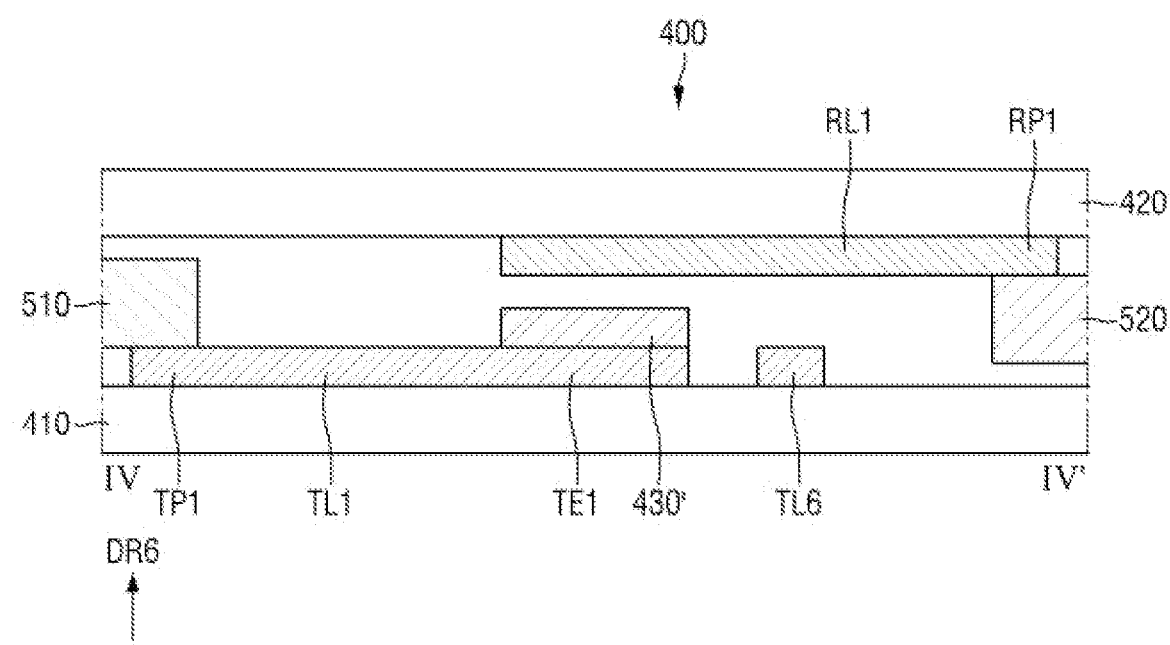

FIGS. 13 and 14 are cross-sectional views illustrating still another example of the force sensor of FIG. 9. FIG. 13 illustrated another example of a cross section of the force sensor taken along line III-III' of FIG. 9, and FIG. 14 illustrated another example of a cross section of the force sensor taken along line IV-IV' of FIG. 9.

The embodiment of FIGS. 13 and 14 is different from the embodiment of FIGS. 10 and 11 in that force sensitive layers 430' respectively contact the force driving electrodes TE1 to TE5 instead of the force sensing electrodes RE1 to RE5. Therefore, a description overlapping with the embodiment of FIGS. 10 and 11 is omitted to avoid redundancy.

Figure 15:
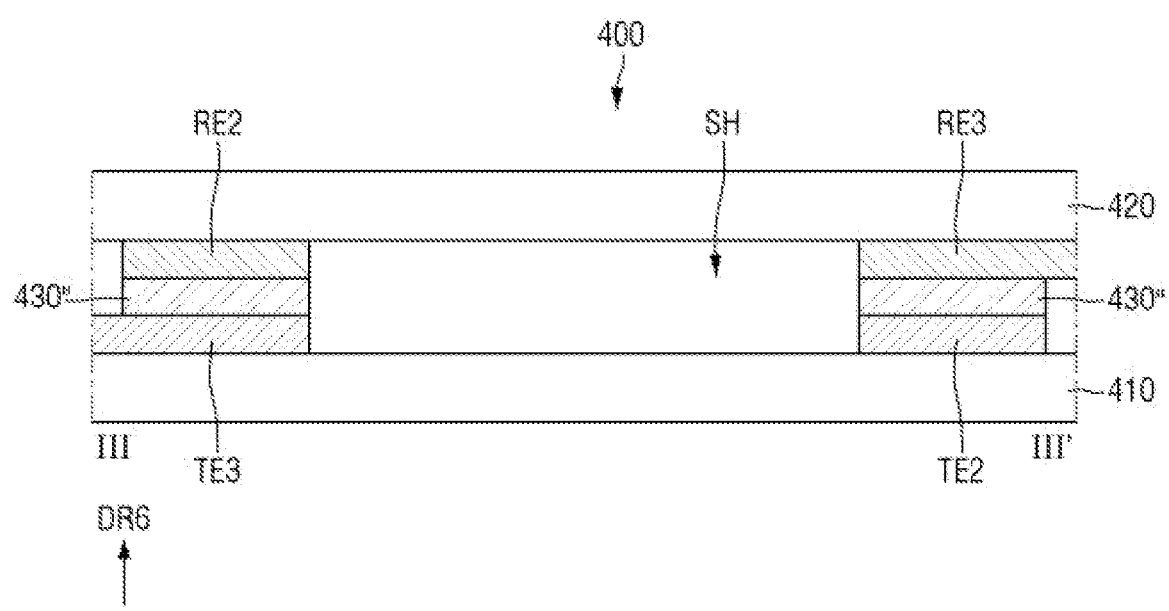
FIGS. 15 and 16 are cross-sectional views illustrating still another example of the force sensor of FIG. 9.
Figure 16:
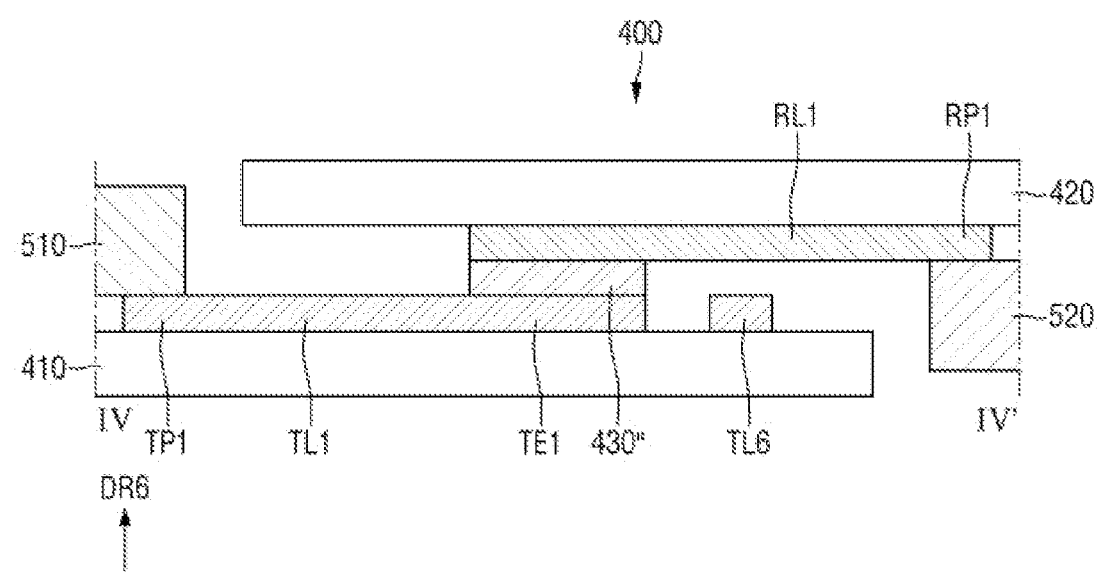

FIGS. 15 and 16 are cross-sectional views illustrating still another example of the force sensor of FIG. 9. FIG. 15 illustrates another example of a cross section of the force sensor taken along line III-III' of FIG. 9, and FIG. 16 illustrates another example of a cross section of the force sensor taken along line IV-IV' of FIG. 9.

The embodiment of FIGS. 15 and 16 is different from the embodiment of FIGS. 10 and 11 in that force sensitive layers 430" contact all the force sensing electrodes RE1 to RE5 and the force driving electrodes TE1 to TE5, respectively. Therefore, a description overlapping with the embodiment of FIGS. 10 and 11 is omitted to avoid redundancy.

Referring to FIGS. 15 and 16, each of the force sensitive layers 430" is a layer made of a dielectric constant modification material whose dielectric constant varies according to the force applied to the force sensor 400, and various materials known in the art may be applied to the force sensitive layers 430". In this case, because the dielectric constant of each force sensitive layer 430" varies according to the force applied to the force sensor 400, capacitance values between the force driving electrodes TE1 to TE5 and the force sensing electrodes RE1 to RE5 are measured, thereby measuring the magnitude of the force applied to the force sensor 400.

Alternatively, the force sensitive layer 430" may include a piezoelectric material having a piezoelectric effect, in which a voltage occurs when a mechanical force is applied, and a reverse piezoelectric effect, in which mechanical deformation occurs when a voltage is applied. For example, the force sensitive layer 430" may include poly vinylidene fluoride (PVDF), plumbum zirconate titanate (PZT), and electroactive polymer (EAP). In this case, the voltage sensed at each of the force sensing electrodes RE1 to RE5 may vary according to the force applied to the force sensor 400 by the piezoelectric effect of each force sensitive layer 430". Therefore, the voltages sensed at the force sensing electrodes RE1 to RE5 may be measured to measure the magnitude of the force applied to the force sensor 400.

Alternatively, the force sensitive layer 430" may be omitted. In this case, distances between the force driving electrodes TE1 to TE5 and the force sensing electrodes RE1 to RE5 may vary according to the force applied to the force sensor 400. Therefore, capacitance values between the force driving electrodes TE1 to TE5 and the force sensing electrodes RE1 to RE5 may be measured to measure the magnitude of the force applied to the force sensor 400.

Figure 17:
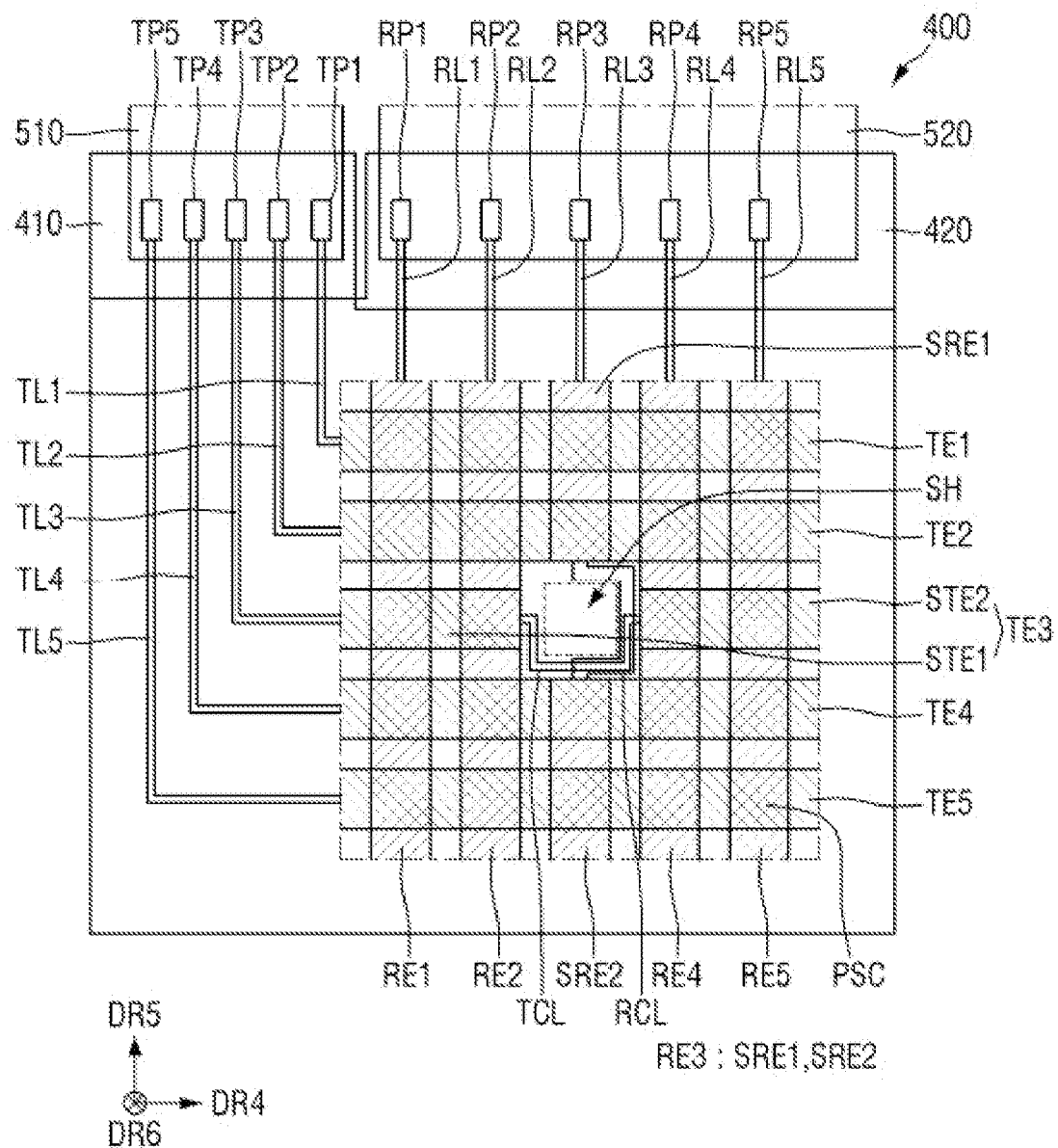
FIG. 17 is a layout view illustrating force sensor electrodes and a sensor hole of a force sensor according to still another embodiment of the invention.

FIG. 17 is a layout view illustrating force sensor electrodes and a sensor hole of a force sensor according to still another embodiment.

The embodiment of FIG. 17 is only different from the embodiment of FIG. 9 in that the first sub-force driving electrode STE1 and the second sub-force driving electrode STE2 are connected through a first force connection wiring, and the first sub-force sensing electrode SRE1 and the second sub-force sensing electrode SRE2 are connected through a second force connection wiring. Therefore, a description overlapping with the embodiment of FIG. 9 is omitted to avoid redundancy. The first force connection wiring may be a driving connection wiring TCL, and the second force connection wiring may be a sensing connection wiring RCL.

Referring to FIG. 17, the third force driving electrode TE3 and the third force sensing electrode RE3 may be removed from the sensor hole SH. Therefore, the first sub-force driving electrode STE1 and the second sub-force driving electrode STE2 of the third force driving electrode TE3 are disconnected from each other by the sensor hole SH, but they may be connected through the driving connection wiring TCL. Further, the first sub-force sensing electrode SRE1 and the second sub-force sensing electrode SRE2 of the third force sensing electrode RE3 are disconnected from each other by the sensor hole SH, but they may be connected through the sensing connection wiring RCL.

The driving connection wiring TCL may be connected to the second side (for example, the right side in FIG. 17) of the first sub-force driving electrode STE1 and the first side (for example, the left side in FIG. 17) of the second sub-force driving electrode STE2. The driving connection wiring TCL may include a plurality of bent portions to bypass the sensor hole SH. For example, the driving connection wiring TCL may extend in the fourth direction DR4, may be bent and extend in the fifth direction DR5, may be bent and extend again in the fourth direction DR4, may be bent and extend again in the fifth direction DR5, and may be bent and extend again in the fourth direction DR4. In order to prevent the area of the sensor hole SH from decreasing by the driving connection wiring TCL, the width of the driving connection wiring TCL may be smaller than the widths of the first sub-force driving electrode STE1 and the second sub-force driving electrode STE2.

The sensing connection wiring RCL may be connected to the fourth side (for example, the lower side in FIG. 17) of the first sub-force sensing electrode SRE1 and the third side (for example, the upper side in FIG. 17) of the second sub-force sensing electrode SRE2. The sensing connection wiring RCL may include a plurality of bent portions to bypass the sensor hole SH. For example, the sensing connection wiring RCL may extend in the fifth direction DR5, may be bent and extend in the fourth direction DR4, may be bent and extend again in the fifth direction DR5, may be bent and extend again in the fourth direction DR4 and may be bent and extend again in the fifth direction DR5. In order to prevent the area of the sensor hole SH from decreasing by the sensing connection wiring RCL, the width of the sensing connection wiring RCL may be smaller than the widths of the first sub-force sensing electrode SRE1 and the second sub-force sensing electrode SRE2. In addition, the driving connection wiring TCL and the sensing connection wiring RCL may overlap each other in the sixth direction DR6, but the inventive concepts are not limited thereto.

The embodiment of FIG. 17 is different from the embodiment of FIG. 9 in that the first side end (for example, the left end in FIG. 17) of the first sub-force driving electrode STE1 is connected to the third force driving wiring TL3, but the second side end (for example, the right end in FIG. 17) of the second sub-force driving electrode STE2 is not connected to any force driving wiring. In addition, the embodiment of FIG. 17 is different from the embodiment of FIG. 9 in that the third side end (for example, the upper end in FIG. 17) of the first sub-force sensing electrode SRE1 is connected to the third force sensing wiring RL3, but the fourth side end (for example, the lower end in FIG. 17) of the second sub-force sensing electrode SRE2 is not connected to any force sensing wiring.

As illustrated in FIG. 17, although the first sub-force driving electrode STE1 and the second sub-force driving electrode STE2 are disconnected by the sensor hole SH, the first and second sub-force driving electrodes STE1 and STE2 may be electrically connected to each other through the driving connection wiring TCL. In addition, although the first sub-force sensing electrode SRE1 and the second sub-force sensing electrode SRE2 are disconnected by the sensor hole SH, the first and second sub-force sensing electrodes SRE1 and SRE2 may be electrically connected to each other through the sensing connection wiring RCL.

Figure 18:
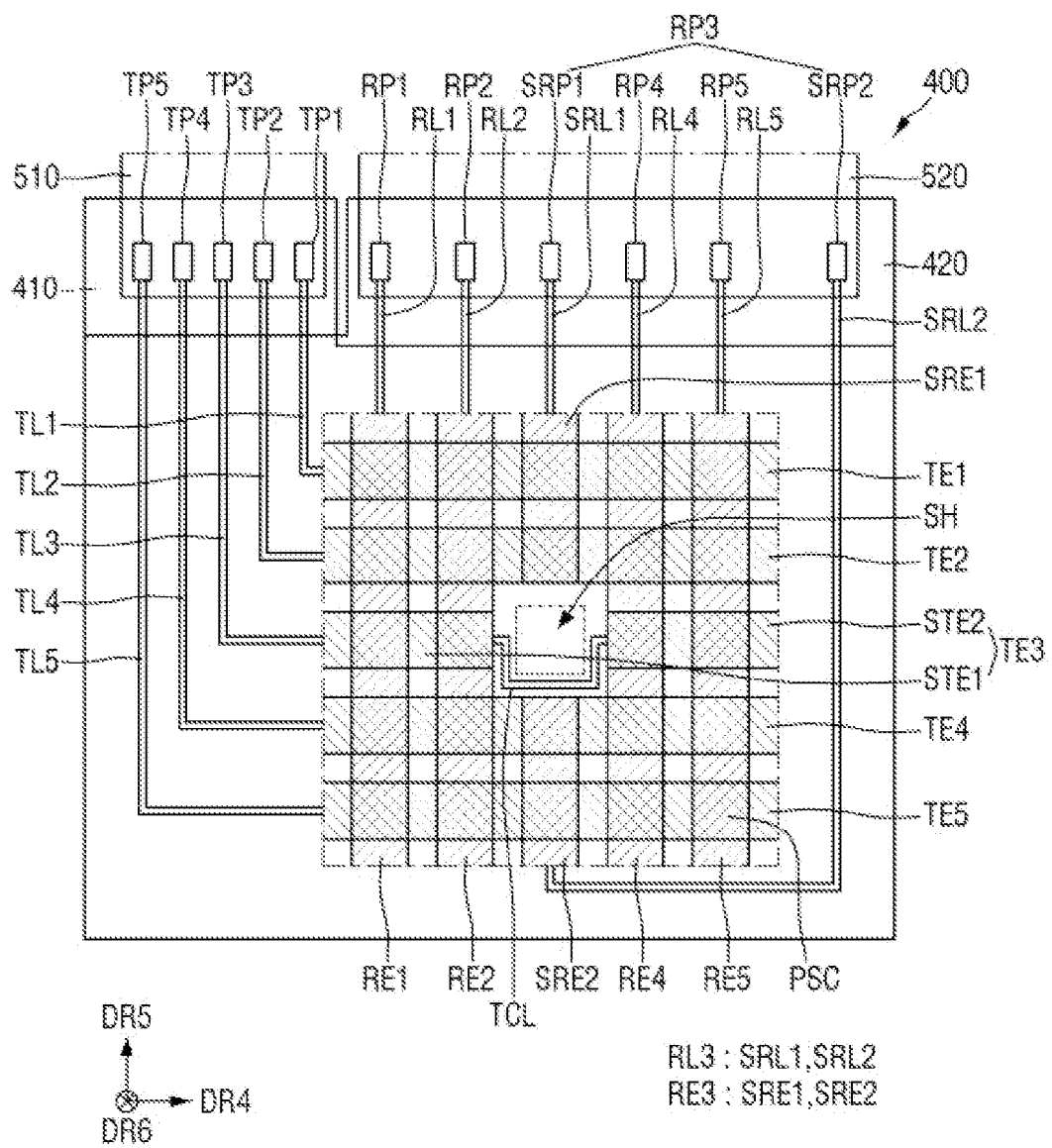
FIG. 18 is a layout view illustrating force sensor electrodes and a sensor hole of a force sensor according to still another embodiment of the invention.

FIG. 18 is a layout view illustrating force sensor electrodes and a sensor hole of a force sensor according to still another embodiment.

The embodiment of FIG. 18 is different from the embodiment of FIG. 9 in that the first sub-force driving electrode STE1 and the second sub-force driving electrode STE2 are connected through the driving connection wiring TCL. Therefore, a description overlapping with the embodiment of FIG. 9 is omitted to avoid redundancy. In addition, because the driving connection wiring TCL connecting the first sub-force driving electrode STE1 to the second sub-force driving electrode STE2 in FIG. 18 is substantially the same as that described with reference to FIG. 17, a description thereof is omitted.

Figure 19:
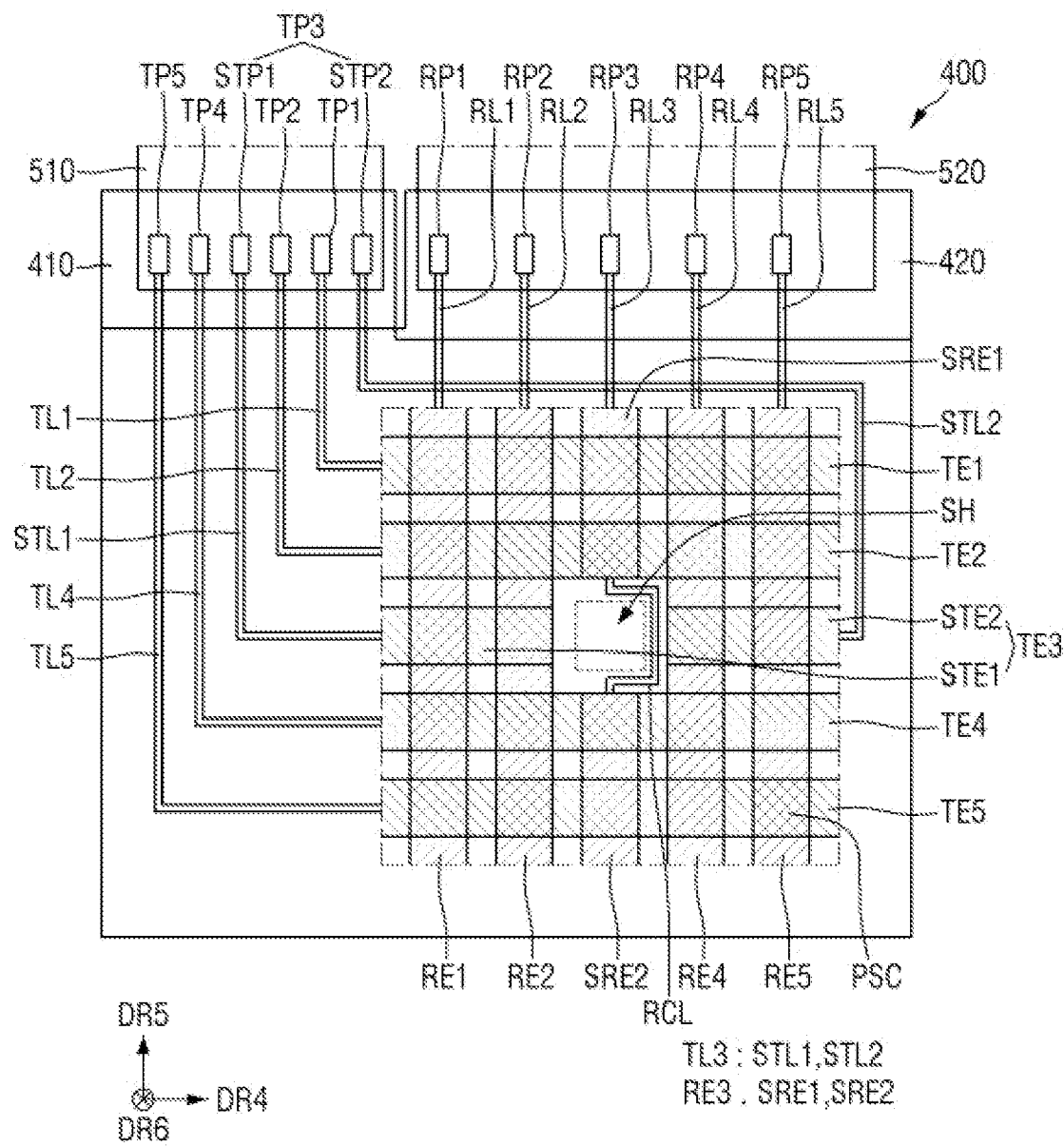
FIG. 19 is a layout view illustrating force sensor electrodes and a sensor hole of a force sensor according to still another embodiment of the invention.

FIG. 19 is a layout view illustrating force sensor electrodes and a sensor hole of a force sensor according to still another embodiment.

The embodiment of FIG. 19 is different from the embodiment of FIG. 9 in that the first sub-force sensing electrode SRE1 and the second sub-force sensing electrode SRE2 are connected through the sensing connection wiring RCL. Therefore, a description overlapping with the embodiment of FIG. 9 is omitted to avoid redundancy. In addition, because the sensing connection wiring RCL connecting the first sub-force sensing electrode SRE1 and the second sub-force sensing electrode SRE2 in FIG. 19 is substantially the same as that described with reference to FIG. 17, a description thereof is omitted.

Figure 20:
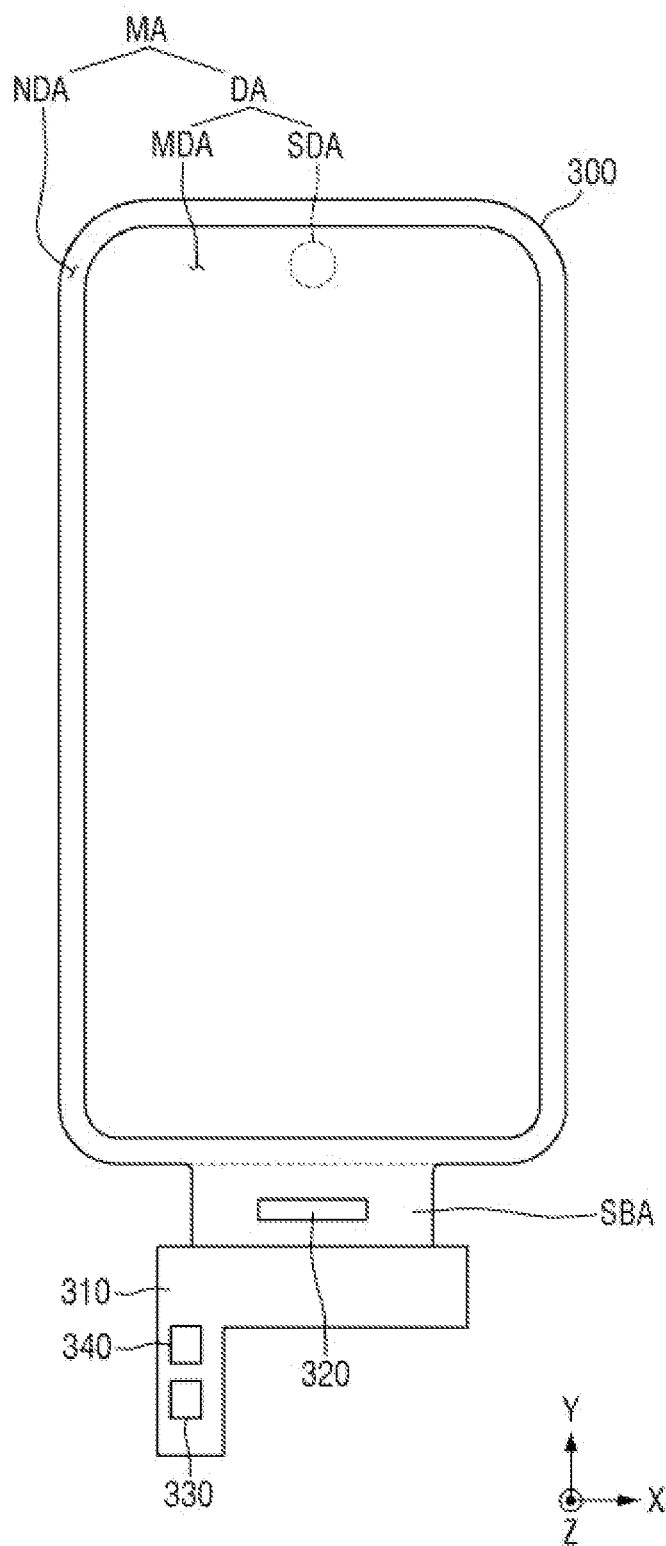
FIG. 20 is a plan view illustrating a display panel, a display circuit board, a display driving circuit, and a touch driving circuit according to still another embodiment of the invention.
Figure 21:
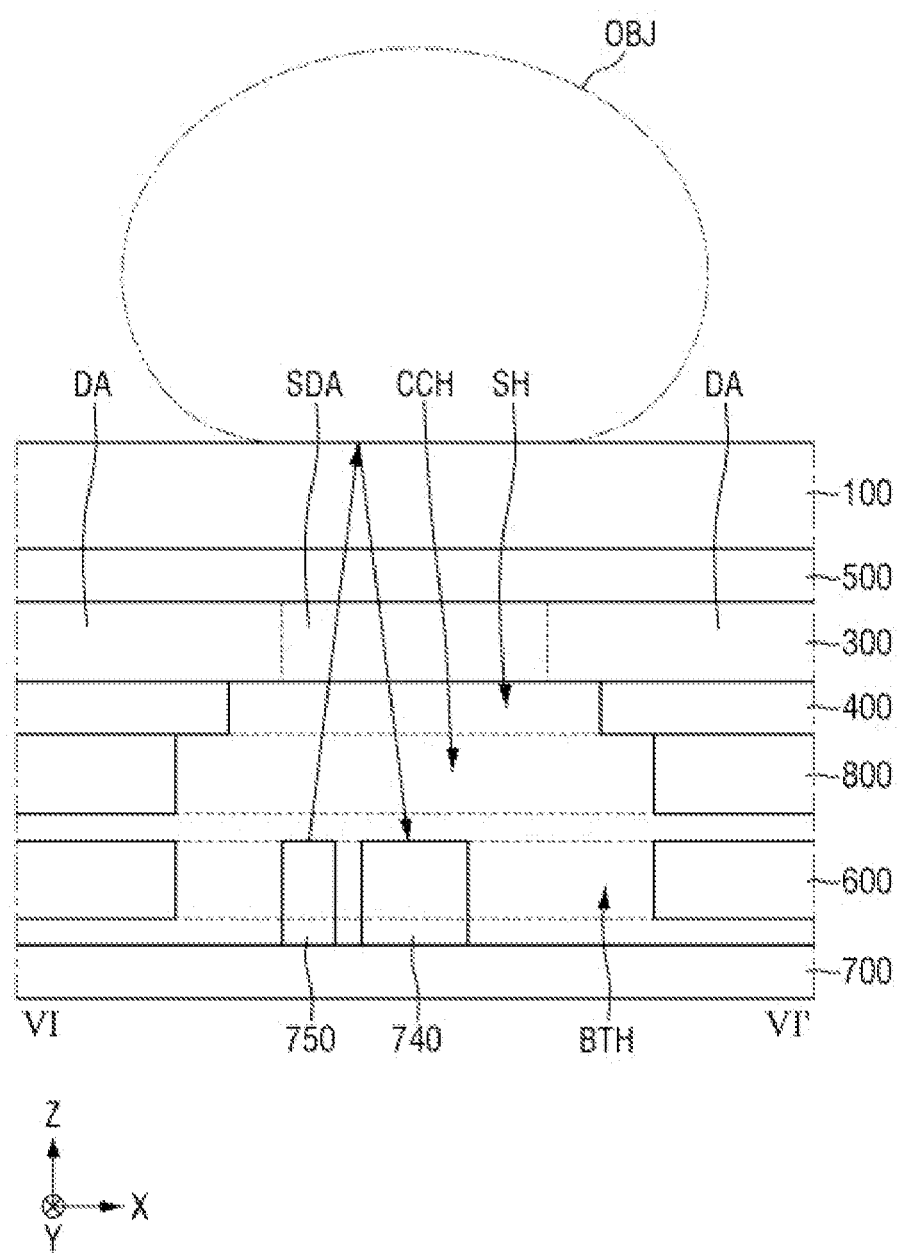
FIG. 21 is a cross-sectional view illustrating a cover window, a display panel, a force sensor, a bottom panel cover, a light emitting unit, and an optical sensor according to still another embodiment of the invention.

FIG. 20 is a plan view illustrating a display panel, a display circuit board, a display driving circuit, and a touch driving circuit according to still another embodiment. FIG. 21 is a cross-sectional view illustrating a cover window, a display panel, a force sensor, a bottom panel cover, a light emitting unit, and an optical sensor according to still another embodiment.

The embodiment of FIGS. 20 and 21 is different from the embodiment of FIGS. 3 and 6 in that the display panel 300 includes a sub-display area SDA instead of the through hole TH.

Referring to FIG. 20, the display area DA of the display panel 300 may include a main display area MDA and the sub-display area SDA. The main display area MDA may occupy most of the display area DA. As noted with regard to FIG. 3, the main region MA may include the display area DA displaying an image and the non-display area NDA that is a peripheral area of the display area DA.

The main display area MDA may not include a transmission area configured to transmit light and may only include a pixel area having pixels configured to display an image. In contrast, the sub-display area SDA may include both the transmission area configured to transmit light and the pixel area having pixels configured to display an image. That is, the sub-display area SDA may include the transmission area as the light transmitting portion capable of passing light. Therefore, the light transmittance of the sub-display area SDA may be higher than that of the main display area MDA.

The sub-display area SDA may be arranged to be surrounded by the main display area MDA. Alternatively, the sub-display area SDA may be arranged to be surrounded by the non-display area NDA, or may be arranged between the display area DA and the non-display area NDA. In addition, although FIG. 20 illustrates that the sub-display area SDA is arranged at the upper center of the display panel 300, the arrangement position of the sub-display area SDA is not limited thereto.

Although FIG. 20 illustrates that the display panel 300 includes one sub-display area SDA, the number of the sub-display areas SDA is not limited thereto. When the display panel 300 includes a plurality of the sub-display areas SDA, any one of the sub-display areas SDA may overlap the optical sensor 740 in the third direction (Z-axis direction), while the other sub-display areas SDA may overlap sensor units other than the optical sensor 740. For example, the sensor unit may be a proximity sensor, illuminance sensor, or front camera sensor.

In addition, although FIG. 20 illustrates that the sub-display area SDA has a circular planar shape, the inventive concepts are not limited thereto. For example, the sub-display area SDA may have a polygonal or elliptical planar shape.

As illustrated in FIGS. 20 and 21, the sub-display area SDA may overlap the sensor hole SH of the force sensor 400, the cover hole CCH of the bottom panel cover 800, the bracket hole BTH of the bracket 600 and the optical sensor 740 in the third direction (Z-axis direction). Therefore, light passing through the sub-display area SDA of the display panel 300 may be incident on the optical sensor 740 through the sensor hole SH. Accordingly, although the optical sensor 740 is disposed under the display panel 300, the optical sensor 740 may sense the light incident from the front surface of the display device 10. For example, light emitted from the light emitting unit 750 may pass through the bracket hole BTH of the bracket 600, the cover hole CCH of the bottom panel cover 800, the sensor hole SH of the force sensor 400 and the sub-display area SDA of the display panel 300 to be absorbed by or reflected from the blood vessels of the user's finger OBJ. The light reflected from the blood vessels of the user's finger OBJ may pass through the sub-display area SDA of the display panel 300, the sensor hole SH of the force sensor 400, the cover hole CCH of the bottom panel cover 800 and the bracket hole BTH of the bracket 600 to be sensed by the optical sensor 740.

Figure 22A:
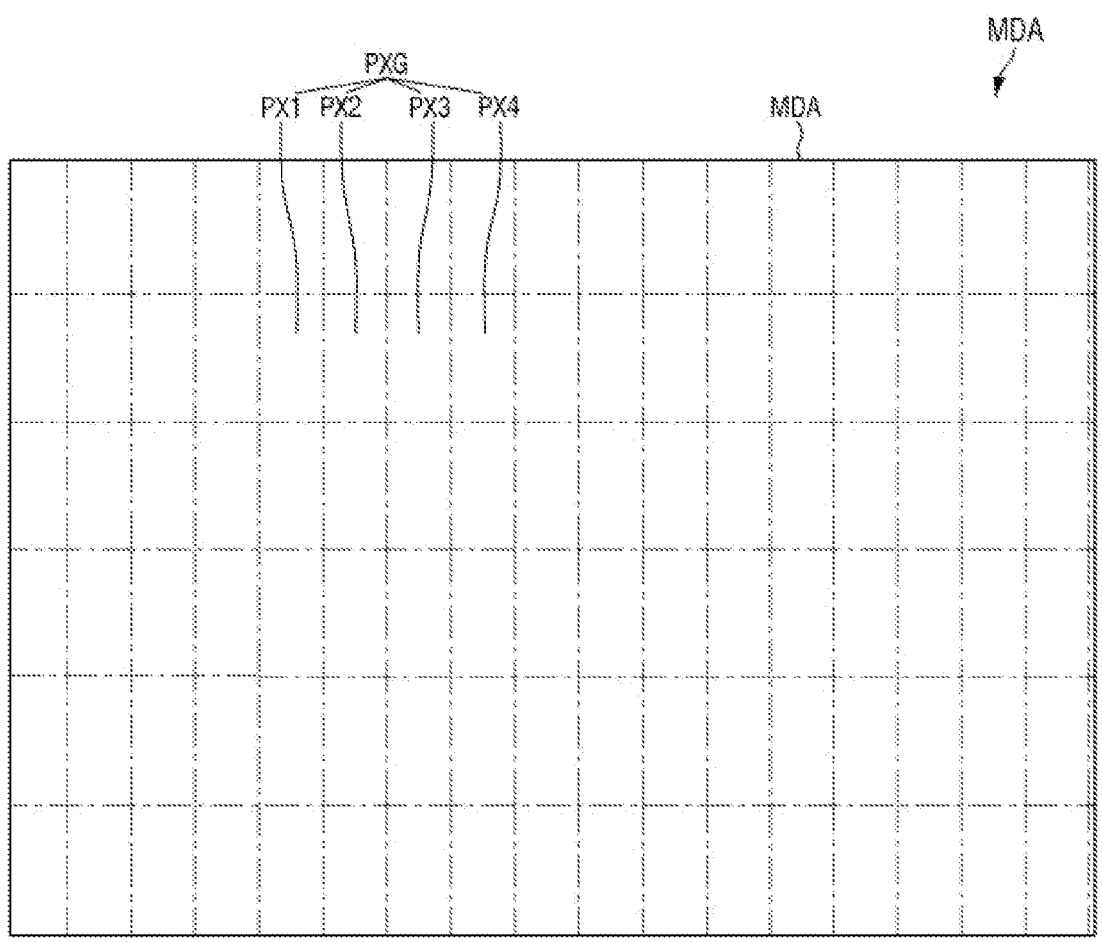
FIGS. 22A and 22B are layout diagrams illustrating a main display area and a sub-display area of a display panel according to an exemplary embodiment of the invention.
Figure 22B:
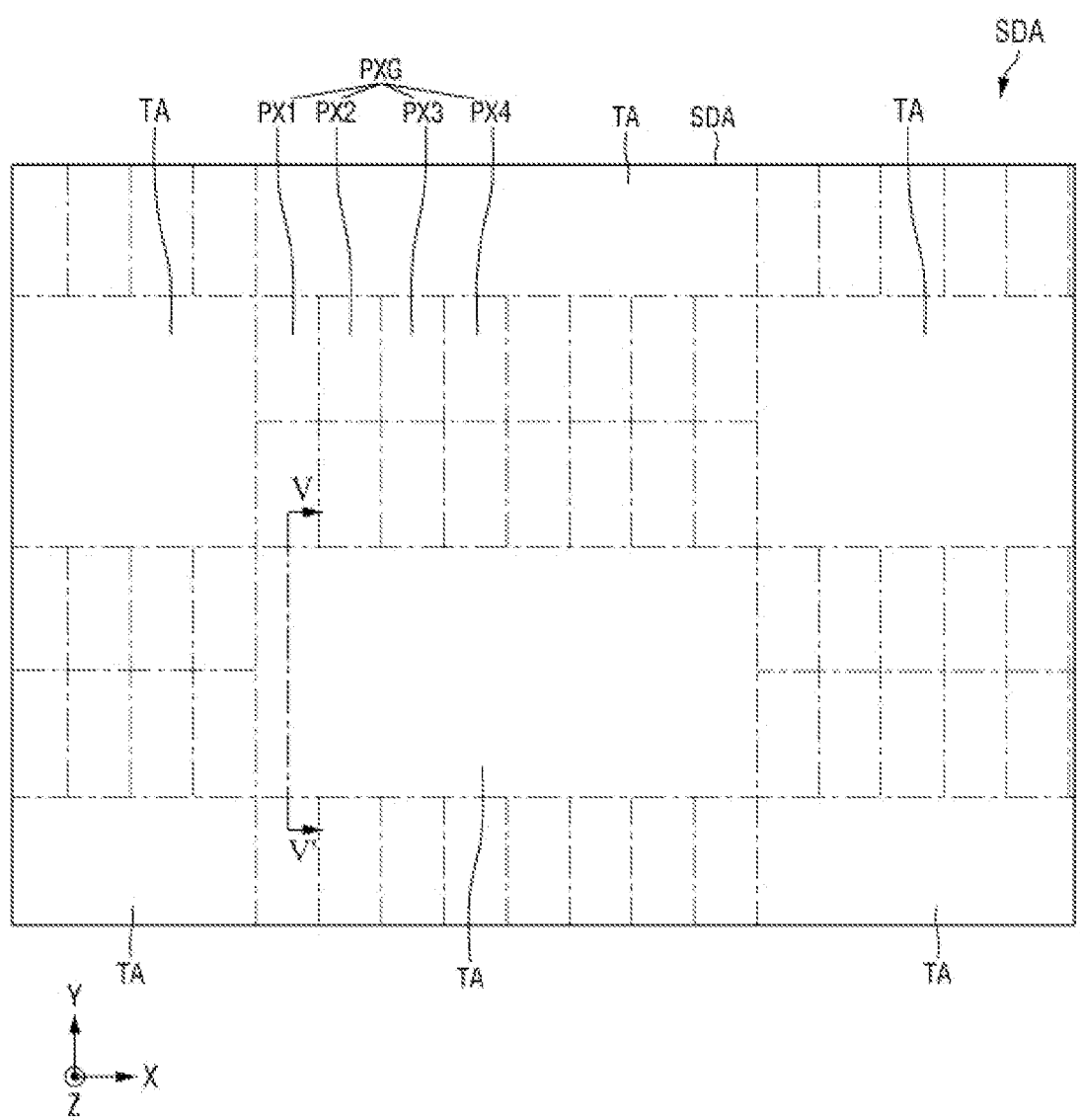

FIG. 22A is a layout diagram illustrating a main display area MDA of a display panel according to an exemplary embodiment. FIG. 22B is a layout diagram illustrating a sub-display area SDA of a display panel according to an exemplary embodiment.

Referring to FIGS. 22A and 22B, the main display area MDA may only include first to fourth pixels PX1 to PX4, while the sub-display area SDA may include pixel areas PXA having the first to fourth pixels PX1 to PX4 and transmission areas TA that transmit light. Accordingly, the number of the pixels PX1 to PX4 per unit area (for example, the number of pixels per inch (PPI)) of the main display area MDA may be more than the number of the pixels PX1 to PX4 per unit area of the sub-display area SDA. For example, the unit area may be an area of a region having a length of one inch in the first direction (X-axis direction) and a length of one inch in the second direction (Y-axis direction).

The pixel areas PXA and the transmission areas TA may be arranged side by side in the first direction (X-axis direction). The pixel areas PXA and the transmission areas TA may be alternately arranged in the first direction (X-axis direction). Further, the pixel areas PXA and the transmission areas TA may be arranged side by side in the second direction (Y-axis direction). The pixel areas PXA and the transmission areas TA may be alternately arranged in the second direction (Y-axis direction).

The number of pixels PX1 to PX4 per unit area of the sub-display area SDA may be less than the number of pixels PX1 to PX4 per unit area of the main display area MDA due to the transmission areas TA. In addition, a ratio of the area of the pixels PX1 to PX4 of the sub-display area SDA to the area of the sub-display area SDA may be smaller than a ratio of the area of the pixels PX1 to PX4 of the main display area MDA to the area of the main display area MDA, due to the transmission areas TA.

Each of the pixel areas PXA may include I (I is a positive integer) pixel groups PXG. For example, each of the pixel areas PXA may include four pixel groups PXG. In this case, two pixel groups PXG may be arrayed in the first direction (X-axis direction) and the other two pixel groups PXG may be arrayed in the second direction (Y-axis direction) in each pixel area PXA. Each of the pixel groups PXG may include the first to fourth pixels PX1 to PX4.

The transmission area TA is an area through which light incident on the display panel 300 passes. The transmission area TA does not include the pixels PX1 to PX4. The transmission area TA may be surrounded by the pixel areas PXA. In order to increase the light transmittance of the transmission area TA, the number of the pixels PX1 to PX4 in the sub-display area SDA may be half the number of the pixels PX1 to PX4 in the main display area MDA excluding the sub-display area SDA. Alternatively, the number of the pixels PX1 to PX4 in the sub-display area SDA may be quarter the number of the pixels PX1 to PX4 in the main display area MDA.

As illustrated in FIGS. 22A and 22B, because the optical sensor 740 overlaps the sub-display area SDA of the display panel 300 including the transmission areas TA in the third direction (Z-axis direction), the optical sensor 740 may sense light incident from the front surface of the display device 10 through the transmission areas TA.

Figure 23:
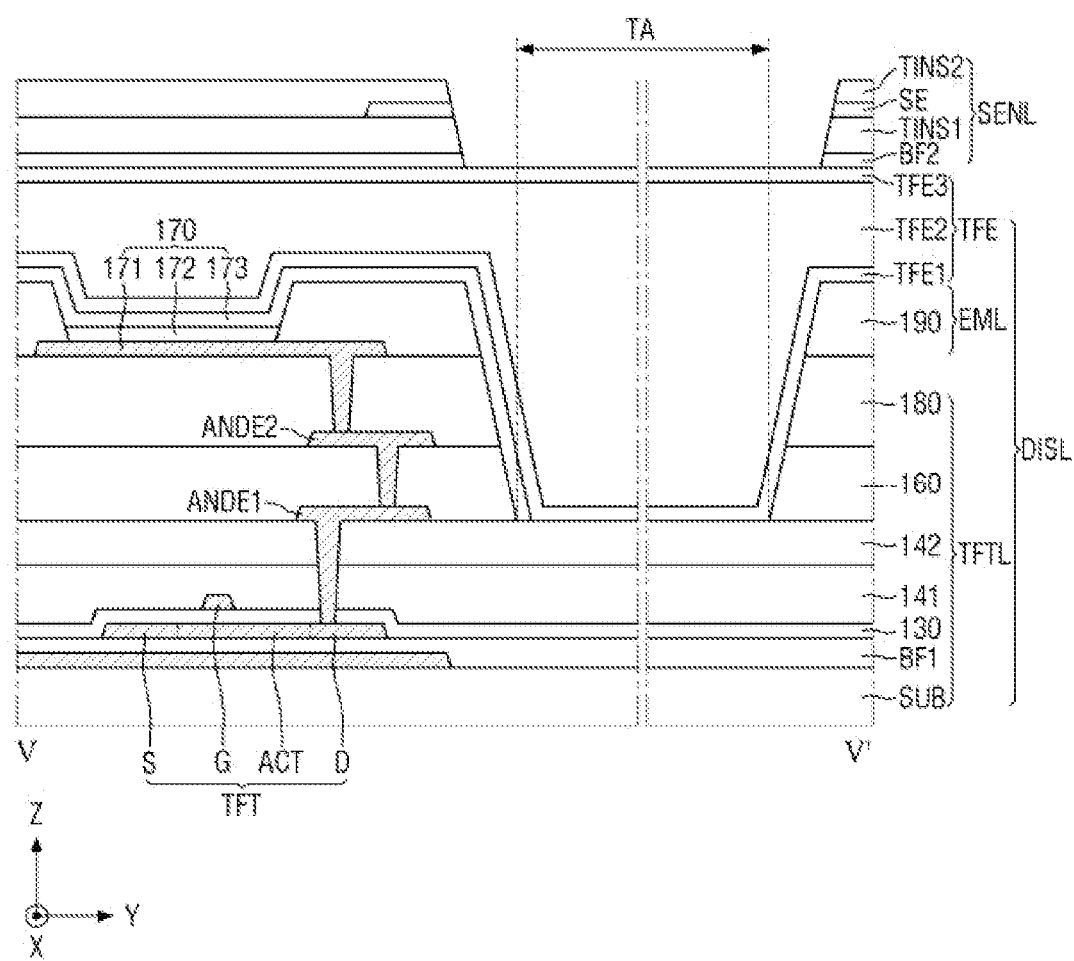
FIG. 23 is a cross-sectional view illustrating an example of the display panel of FIG. 22B.

FIG. 23 is a cross-sectional view illustrating an example of the display panel of FIG. 22B. FIG. 23 illustrates a cross section of the display panel 300 taken along line V-V' of FIG. 22B.

In the embodiment of FIG. 23, the substrate SUB, the thin film transistor layer TFTL, and the sensor electrode layer SENL formed in the display area DA may be substantially the same as those described with reference to FIG. 8 except for the transmission area TA. Therefore, a description thereof is omitted.

Referring to FIG. 23, the transmission area TA may be an area, in which metal layers of the thin film transistor layer TFTL, the light emitting element layer EML, and the sensor electrode layer SENL are not disposed, to transmit light. Therefore, the transmission area TA may include a first substrate SUB1, the first buffer film BF1, a second substrate SUB2, the second buffer film BF2, the gate insulating film 130, the first interlayer insulating film 141, the second interlayer insulating film 142, the first inorganic film TFE1, the organic film TFE2, and the second inorganic film TFE3.

The first planarization film 160, the second planarization film 180, and the bank 190 may be removed from the transmission area TA. In addition, the encapsulation layer TFE may fill the region of the transmission area TA from which the first planarization film 160, the second planarization film 180, and the bank 190 have been removed. For example, the first inorganic film TFE1 and the organic film TFE2 may fill the region of the transmission area TA from which the first planarization film 160, the second planarization film 180, and the bank 190 have been removed. Therefore, the first inorganic film TFE1 and the second interlayer insulating film 142 may contact each other in the transmission area TA.

FIG. 23 illustrates that the first planarization film 160, the second planarization film 180, and the bank 190 are removed from the transmission area TA, but the inventive concepts are not limited thereto. For example, at least one of the first buffer film BF1, the gate insulating film 130, the first interlayer insulating film 141, or the second interlayer insulating film 142 may be further removed from the transmission area TA.

As illustrated in FIG. 23, because the opaque material is not disposed in the transmission area TA, light passing through the transmission area TA may be incident on the optical sensor 740 which overlaps the sub-display area SDA including the transmission area TA in the third direction (Z-axis direction).

Figure 24:
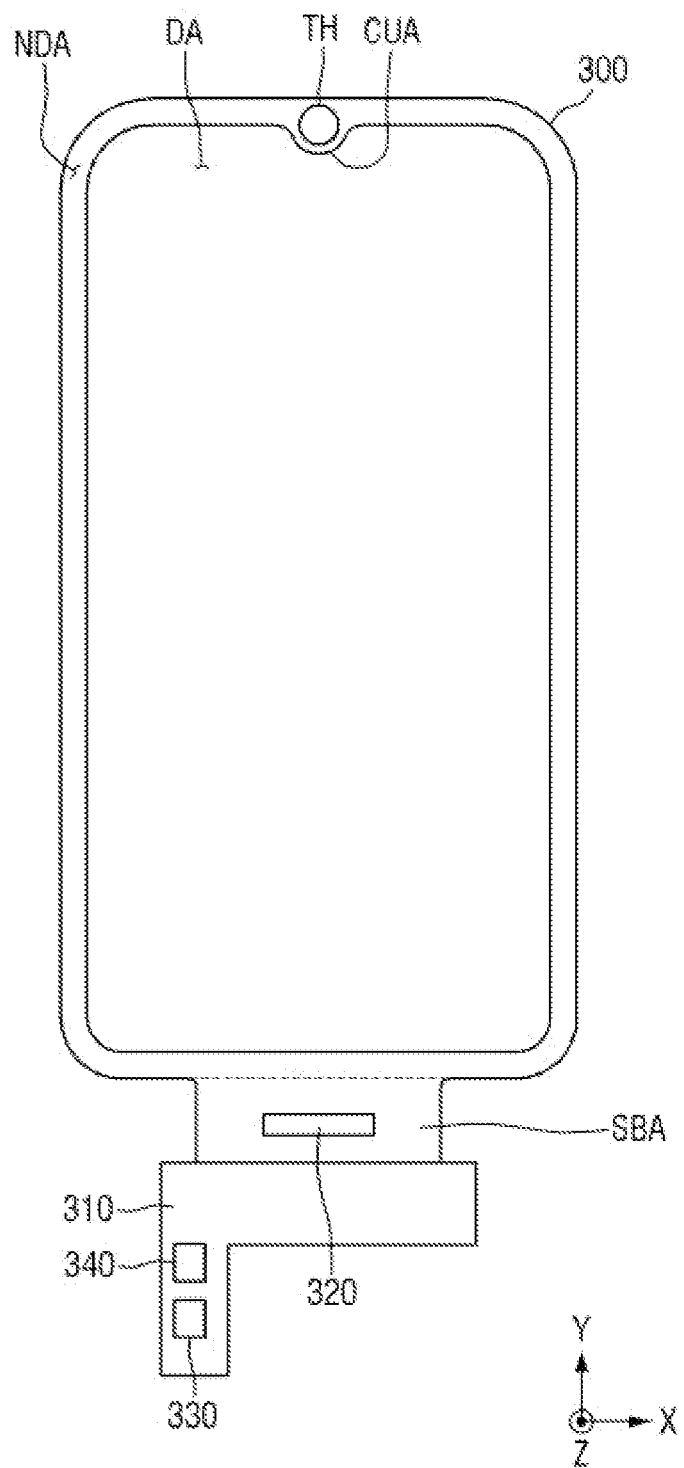
FIG. 24 is a plan view illustrating a display panel, a display circuit board, a display driving circuit, and a touch driving circuit according to still another embodiment of the invention.

FIG. 24 is a plan view illustrating a display panel, a display circuit board, a display driving circuit, and a touch driving circuit according to still another embodiment.

The embodiment of FIG. 24 is different from the embodiment of FIG. 3 in that the through hole TH of the display panel 300 is arranged to be surrounded by the non-display area NDA. Therefore, a description overlapping with the embodiment of FIG. 3 is omitted to avoid redundancy.

Referring to FIG. 24, the through hole TH may be arranged to be surrounded by the non-display area NDA. In this case, when the length of the through hole TH in the second direction (Y-axis direction) is greater than the length of the non-display area NDA in the second direction (Y-axis direction), the display area DA may include a recess portion CUA concavely curved from a region where the through hole TH is formed, thereby avoiding the through hole TH.

Figure 25:
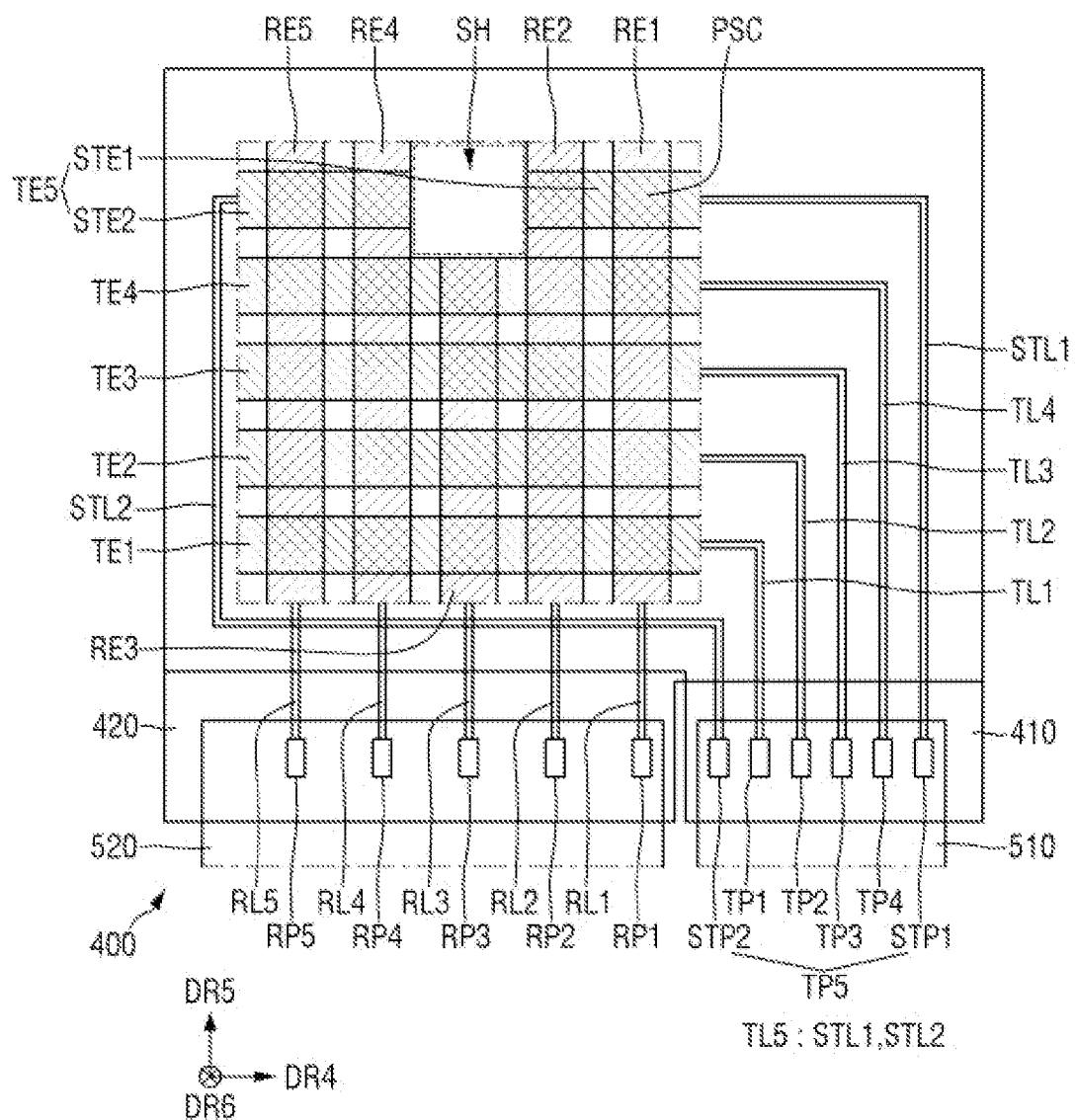
FIG. 25 is a layout view illustrating force sensor electrodes and a sensor hole of a force sensor according to still another embodiment of the invention.

FIG. 25 is a layout view illustrating force sensor electrodes and a sensor hole of a force sensor according to still another embodiment.

The embodiment of FIG. 25 is different from the embodiment of FIG. 9 in that the sensor hole SH of the force sensor 400 is arranged at one edge of the force sensor 400. Therefore, a description overlapping with the embodiment of FIG. 9 is omitted to avoid redundancy.

Referring to FIG. 25, when the through hole TH is arranged at one edge of the display panel 300 as illustrated in FIG. 24, the sensor hole SH of the force sensor 400 may be also arranged at one edge of the force sensor 400. For example, the sensor hole SH may be arranged at the third side (for example, the upper side in FIG. 25) of the force sensor 400, and the force driving pads TP1 to TP5 and the force sensing pads RP1 to RP5 may be arranged at the fourth side (for example, the lower side in FIG. 25) of the force sensor 400. The sensor hole SH may be the light transmitting portion that passes light as illustrated in FIG. 10, but the inventive concepts are not limited thereto. The sensor hole SH may be a physical hole, which is physically formed, as illustrated in FIG. 12.

The force sensor 400 may include the first sub-force driving electrode STE1 and the second sub-force driving electrode STE2 which are divided from the fifth force driving electrode TE5 by the sensor hole SH instead of the third force driving electrode TE3. The first sub-force driving electrode STE1 may be disposed on the second side (for example, the right side in FIG. 25) of the sensor hole SH, and the second sub-force driving electrode STE2 may be disposed on the first side (for example, the left side in FIG. 25) of the sensor hole SH.

Because the first sub-force driving electrode STE1 and the second sub-force driving electrode STE2 are disconnected by the sensor hole SH, the first sub-force driving electrode STE1 and the second sub-force driving electrode STE2 may be connected to the sub-force driving wirings STL1 and STL2, respectively. For example, the fifth force driving wiring TL5 may include the first sub-force driving wiring STL1 connected to the first sub-force driving electrode STE1 and the second sub-force driving wiring STL2 connected to the second sub-force driving electrode STE2. The first sub-force driving wiring STL1 may connect the first sub-force driving electrode STE1 to the first sub-force driving pad STP1 of the fifth force driving pad TP5. The second sub-force driving wiring STL2 may connect the second sub-force driving electrode STE2 to the second sub-force driving pad STP2 of the fifth force driving pad TP5.

The first to fourth force driving electrodes TE1 to TE4 and the first sub-force driving electrode STE1 may be respectively connected to the first to fourth force driving wirings TL1 to TL4 and the first sub-force driving wiring STL1 at the second side ends (for example, the right ends in FIG. 25) thereof. In contrast, the second sub-force driving electrode STE2 may be connected to the second sub-force driving wiring STL2 at the first side end (for example, the left side end in FIG. 25) thereof. Because the second sub-force driving wiring STL2 is connected to the second sub-force driving pad STP2 after passing through the left portion and the lower portion of the force sensor 400, the second sub-force driving wiring STL2 may cross the first to fifth force sensing electrodes RE1 to RE5 at the lower side of the force sensor 400.

Because the third force sensing electrode RE3 is partially removed by the sensor hole SH, the length of the third force sensing electrode RE3 in the fifth direction DR5 may be smaller than the length of each of the force sensing electrodes RE1, RE2, RE4, and RE5 in the fifth direction DR5 except for the third force sensing electrode RE3 among the first to fifth force sensing electrodes RE1 to RE5.

Further, the embodiment of FIG. 25 is different from the embodiment of FIG. 9 in that the first to fourth force driving electrodes TE1 to TE4 and the first sub-force driving electrode STE1 are respectively connected to the first to fourth force driving wirings TL1 to TL4 and the first sub-force driving wiring STL1 at the second side ends (for example, the right ends in FIG. 25) thereof and the second sub-force driving electrode STE2 is connected to the second sub-force driving wiring STL2 at the first side end (for example, the left end in FIG. 25) thereof. Further, the embodiment of FIG. 25 is different from the embodiment of FIG. 9 in that the fifth force sensing electrode RE5 is not divided by the sensor hole SH, and the first to fifth force sensing electrodes RE1 to RE5 are respectively connected to the first to fifth force sensing wirings RL1 to RL5 at the fourth side ends (for example, the lower ends in FIG. 25) thereof.

As illustrated in FIG. 25, although the first sub-force driving electrode STE1 and the second sub-force driving electrode STE2 are disconnected by the sensor hole SH, the first and second sub-force driving electrodes STE1 and STE2 may be respectively connected to the sub-force driving wirings STL1 and STL2 to be electrically connected to the force driving circuit 340.

Figure 26:
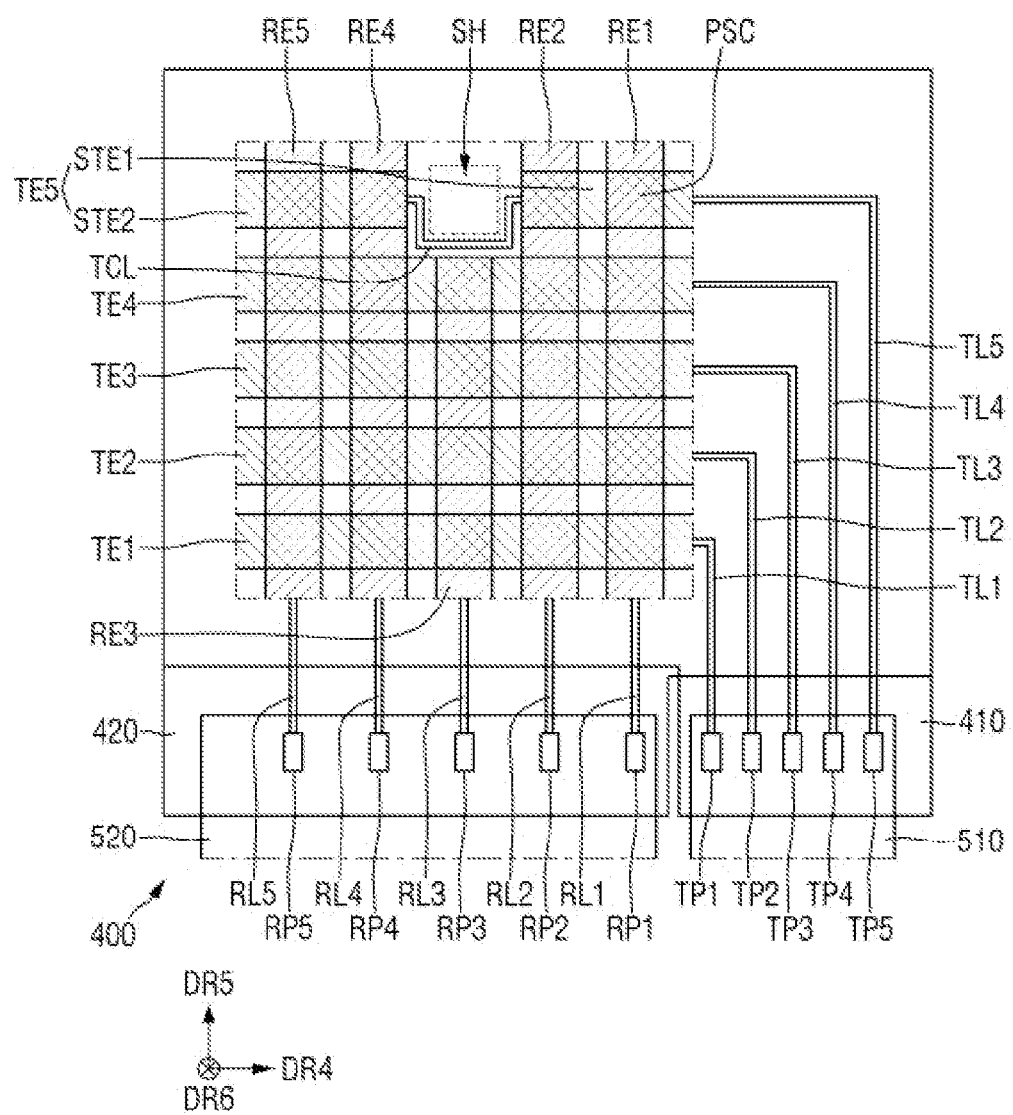
FIG. 26 is a layout view illustrating force sensor electrodes and a sensor hole of a force sensor according to still another embodiment of the invention.

FIG. 26 is a layout view illustrating force sensor electrodes and a sensor hole of a force sensor according to still another embodiment.

The embodiment of FIG. 26 is different from the embodiment of FIG. 25 in that the first sub-force driving electrode STE1 and the second sub-force driving electrode STE2 are connected through the driving connection wiring TCL. Therefore, a description overlapping with the embodiment of FIG. 25 is omitted to avoid redundancy.

Referring to FIG. 26, the fifth force driving electrode TE5 and the third force sensing electrode RE3 may be removed from the sensor hole SH. Therefore, the first sub-force driving electrode STE1 and the second sub-force driving electrode STE2 of the fifth force driving electrode TE5 are disconnected from each other by the sensor hole SH, but they may be connected through the driving connection wiring TCL.

The driving connection wiring TCL may be connected to the first side (for example, the left side in FIG. 26) of the first sub-force driving electrode STE1 and the second side (for example, the right side in FIG. 26) of the second sub-force driving electrode STE2. The driving connection wiring TCL may include a plurality of bent portions to bypass the sensor hole SH. For example, the driving connection wiring TCL may extend in the fourth direction DR4, may be bent and extend in the fifth direction DR5, may be bent and extend again in the fourth direction DR4, may be bent and extend again in the fifth direction DR5, and may be bent and extend again in the fourth direction DR4. In order to prevent the area of the sensor hole SH from decreasing by the driving connection wiring TCL, the width of the driving connection wiring TCL may be smaller than the widths of the first sub-force driving electrode STE1 and the second sub-force driving electrode STE2.

The embodiment of FIG. 26 is different from the embodiment of FIG. 25 in that the second side end (for example, the right end in FIG. 26) of the first sub-force driving electrode STE1 is connected to the fifth force driving wiring TL5, while the first side end (for example, the left end in FIG. 26) of the second sub-force driving electrode STE2 is not connected any force driving wiring.

As illustrated in FIG. 26, although the first sub-force driving electrode STE1 and the second sub-force driving electrode STE2 are disconnected by the sensor hole SH, the first and second sub-force driving electrodes STE1 and STE2 may be electrically connected through the driving connection wiring TCL.

Figure 27:
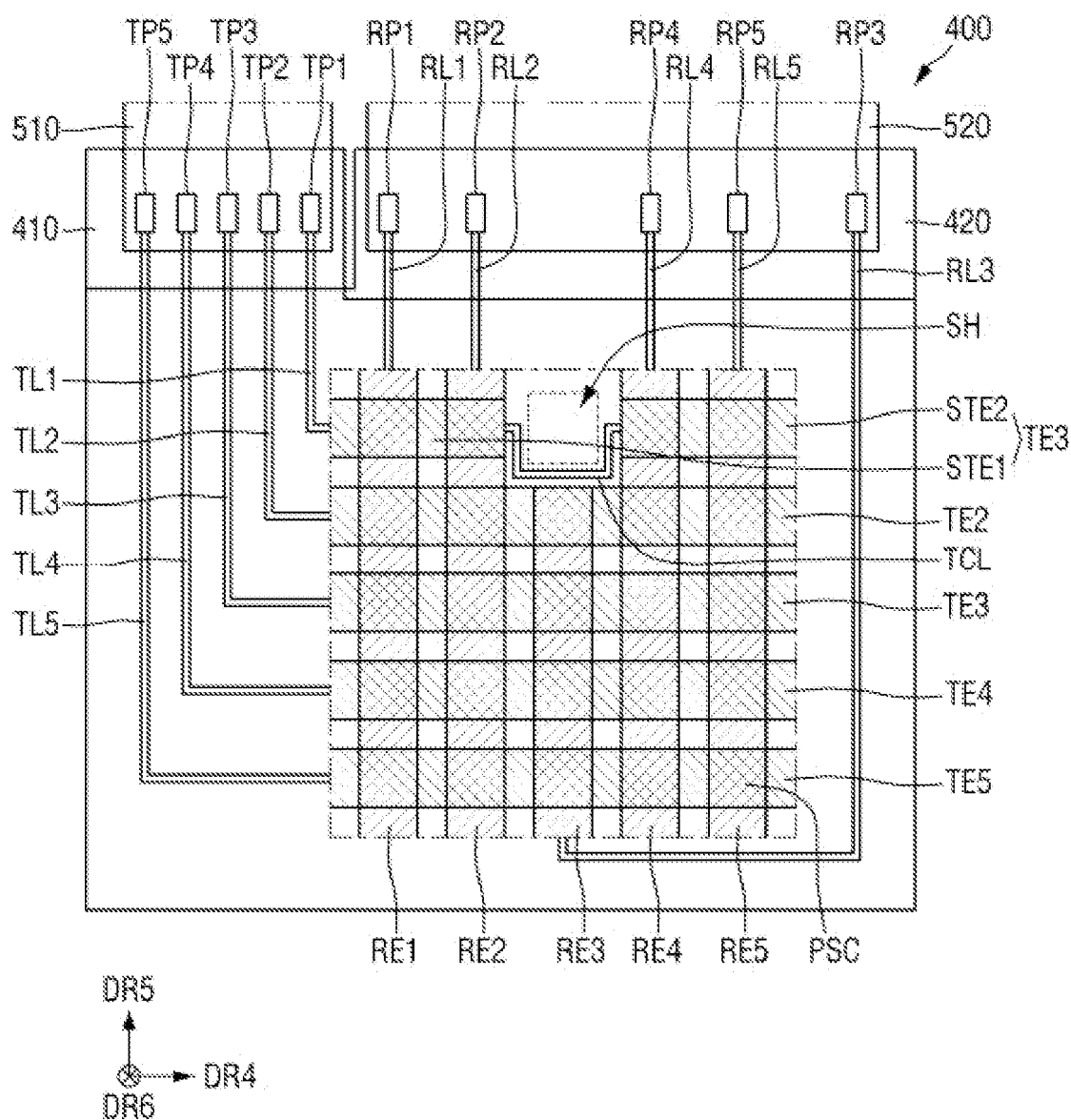
FIG. 27 is a layout view illustrating force sensor electrodes and a sensor hole of a force sensor according to still another embodiment of the invention.

FIG. 27 is a layout view illustrating force sensor electrodes and a sensor hole of a force sensor according to still another embodiment.

The embodiment of FIG. 27 is different from the embodiment of FIG. 26 in that all of the sensor hole SH, the force driving pads TP1 to TP5 and the force sensing pads RP1 to RP5 are disposed at another side of the force sensor 400. Therefore, a description overlapping with the embodiment of FIG. 26 is omitted to avoid redundancy.

Meanwhile, the sensor hole SH illustrated in FIGS. 25 to 27 may be replaced with a notch portion that one side of the force sensor 400 is concavely recessed.

Figure 28:
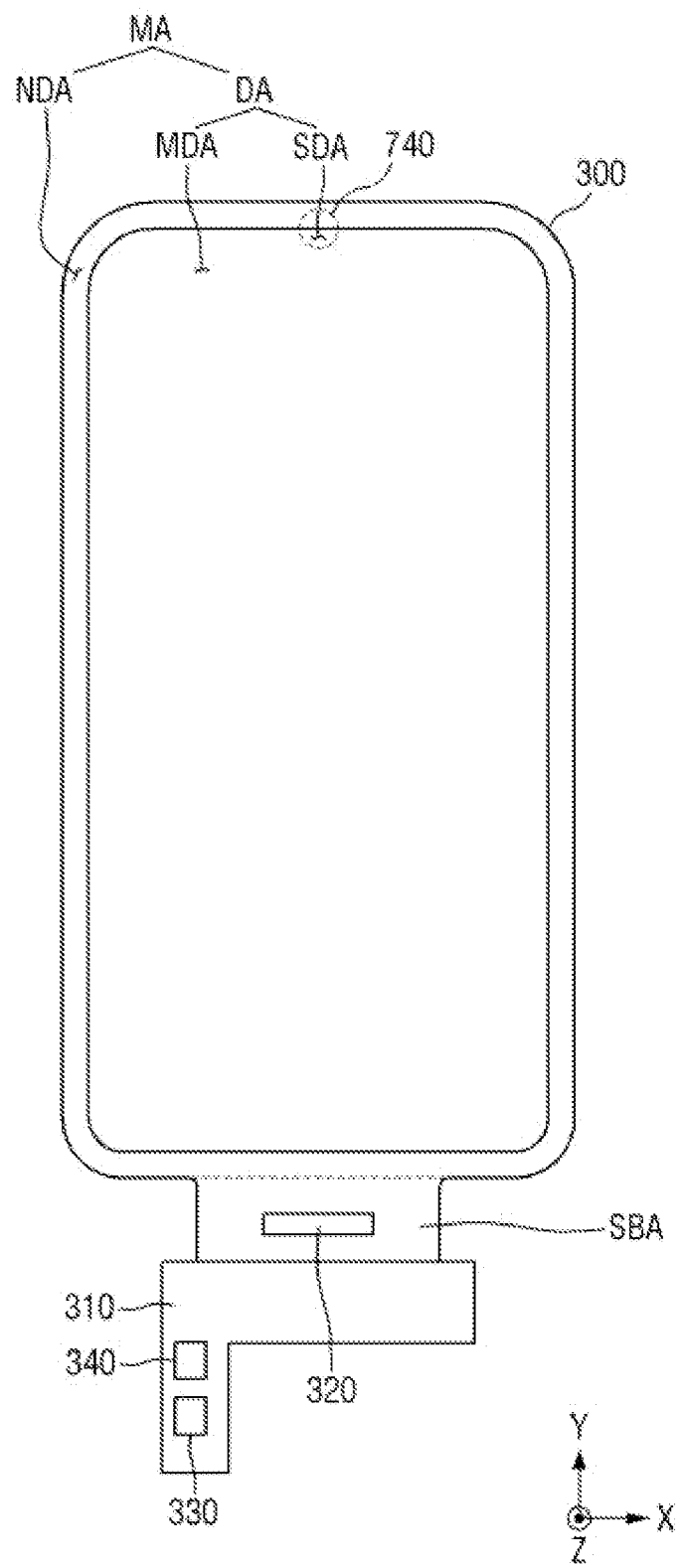
FIG. 28 is a plan view illustrating a display panel, a display circuit board, a display driving circuit, and a touch driving circuit according to still another embodiment of the invention.

FIG. 28 is a plan view illustrating a display panel, a display circuit board, a display driving circuit, and a touch driving circuit according to still another embodiment.

The embodiment of FIG. 28 is different from the embodiment of FIG. 20 in that the sub-display area SDA of the display panel 300 is arranged to be surrounded by the display area DA and the non-display area NDA. Therefore, a description overlapping with the embodiment of FIG. 20 is omitted to avoid redundancy.

Referring to FIG. 28, when the optical sensor 740 is arranged across both the display area DA and the non-display area NDA at the boundary between the display area DA and the non-display area NDA, the sub-display area SDA may overlap a region where the optical sensor 740 is disposed in the display area DA, in the third direction (Z-axis direction). A part of the sub-display area SDA may be adjacent to the display area DA, and the remaining part of the sub-display area SDA may be adjacent to the non-display area NDA. The sub-display area SDA is illustrated to have a semicircular planar shape, but the inventive concepts are not limited thereto. For example, the sub-display area SDA may be formed in a polygonal shape or an oval shape.

As illustrated in FIG. 28, when the sub-display area SDA is arranged at one edge of the display panel 300, the sensor hole SH of the force sensor 400 may be also arranged at one edge of the force sensor 400 as illustrated in FIGS. 25 to 27.

Figure 29:
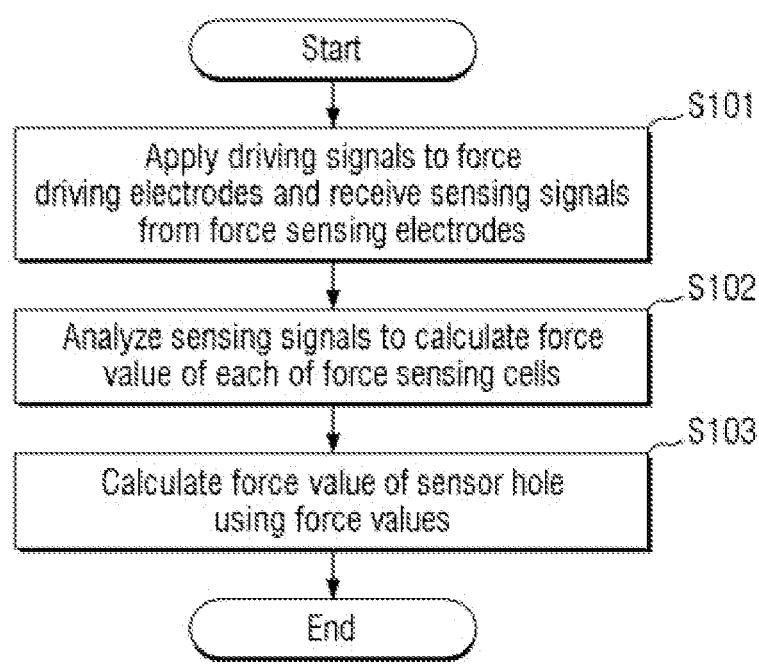
FIG. 29 is a flowchart illustrating a method of calculating a force value of the hole formed in the force sensor according to an exemplary embodiment of the invention.

FIG. 29 is a flowchart illustrating a method of calculating a force value of the hole formed in the force sensor according to an exemplary embodiment.

First, as in a first operation S101 of FIG. 29, the force driving circuit 340 may sequentially apply driving signals to the force driving electrodes TE1 to TE5 of the force sensor 400 through the force driving circuit board 510 and may receive sensing signals from the force sensing electrodes RE1 to RE5 of the force sensor 400 through the force sensing circuit board 520.

Specifically, when a force is applied to the force sensor 400, the force sensitive layer 430 contacts the force driving electrode and the force sensing electrode. Accordingly, a current may flow from the force driving electrode to the force sensing electrode through the force sensitive layer 430. The force driving circuit 340 may receive a current or voltage applied from the force sensing electrode as the sensing signal.

Second, as in a second operation S102 of FIG. 29, the force driving circuit 340 may analyze the sensing signals to calculate the force value of each of the force sensing cells PSC disposed in the crossing regions of the force driving electrodes TE1 to TE5 and the force sensing electrodes RE1 to RE5.

The force driving circuit 340 may receive a current or voltage applied from each of the force sensing electrodes as the sensing signal to calculate electrical resistance of each of the force sensing cells PSC according to the sensing signal. Because the force value decreases as the electrical resistance of the force sensing cell PSC increases, the force driving circuit 340 may calculate the force value according to the electrical resistance of each force sensing cell PSC by using a pre-stored lookup table or performing an algorithm.

Third, as in a third operation S103 of FIG. 29, the force driving circuit 340 may output the force values to the main processor 710. The main processor 710 may calculate the force value of the sensor hole SH using the force values. Alternatively, the force driving circuit 340 may calculate the force value of the sensor hole SH using the force values before outputting the force values to the main processor 710.

The force sensor 400 may include the sensor hole SH configured to guide light incident from the through hole TH or the sub-display area SDA of the display panel 300 to the optical sensor 740. Because the third force driving electrode TE3 and the third force sensing electrode RE3 are removed from the sensor hole SH, the force driving circuit 340 may estimate the force value of the sensor hole SH of the force sensor 400. The force driving circuit 340 may calculate the force values of the force sensing cells PSC around the sensor hole SH as illustrated in FIG. 30.

The force driving circuit 340 may calculate the force value of the sensor hole SH in consideration of the distribution of the force values of the force sensing cells PSC arranged around the sensor hole SH. For example, the force driving circuit 340 may analyze force values of 184 and 120 arranged in the fourth direction DR4, force values of 273 and 188 arranged in the fifth direction DR5, force values of 198 and 88 arranged in a first diagonal direction DR7, and force values of 146 and 210 arranged in a second diagonal direction DR8 intersecting the first diagonal direction DR7, among the force values of the force sensing cells PSC disposed around the sensor hole SH. Accordingly, it is possible to grasp the tendency of the force values of the force sensing cells PSC disposed around the sensor hole SH, thereby calculating the force value of the sensor hole SH.

Alternatively, the force driving circuit 340 may calculate the average value or the median value of the force values of the force sensing cells PSCs disposed around the sensor hole SH, as the force value of the sensor hole SH. Alternatively, when the user measures a blood pressure, it is highly likely that the user presses the display device 10 after positioning the central region of the finger OBJ above the sensor hole SH. Therefore, it is very likely that the force value of the sensor hole SH may be greater than the force values of the force sensing cells PSC disposed around the sensor hole SH. Accordingly, the force driving circuit 340 may calculate, as the force value of the sensor hole SH, the average value or the median value of N (N is a positive integer equal to or greater than 2) upper force values among the force values of the force sensing cells PSC disposed around the sensor hole SH.

Alternatively, the force driving circuit 340 may calculate the sum of the force values to determine the force value of the sensor hole SH using a lookup table storing the force value of the sensor hole SH calculated in advance according to the sum of the force values.

Figure 32:
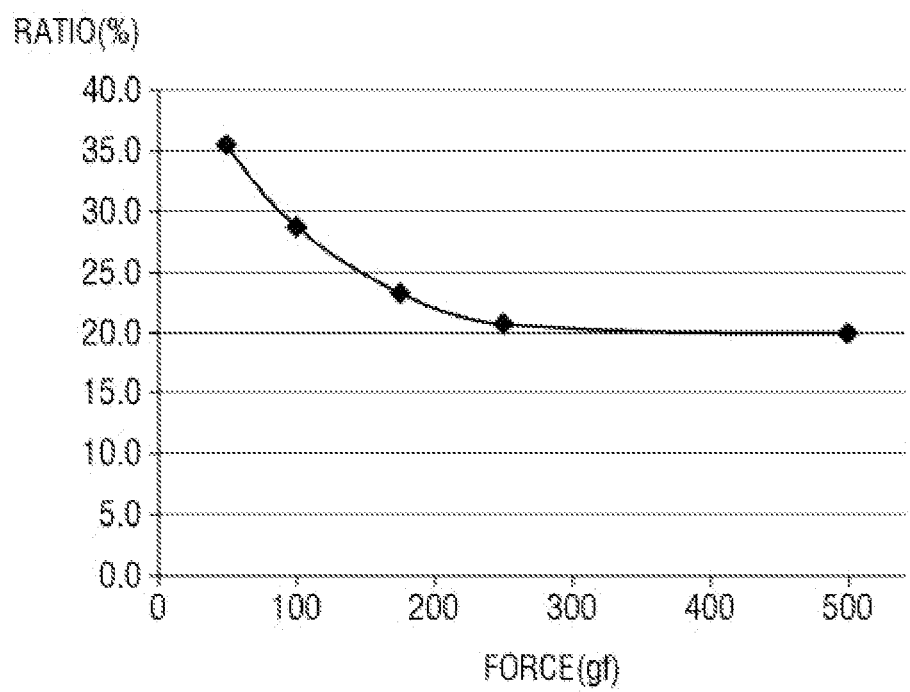
FIG. 32 is a graph illustrating an example of a ratio of the force value of the sensor hole to the sum of the force values of the force sensor according to the amount of the force applied to the force sensor according to an exemplary embodiment of the invention.

Specifically, the sum of the force values calculated from the force sensor 400 including the sensor hole SH as illustrated in FIG. 30 may be subtracted from the sum of force values calculated from the force sensor 400' not including the sensor hole SH as illustrated in FIG. 31, thereby calculating the force value of the sensor hole SH. However, as illustrated in FIG. 32, a ratio of the force value of the sensor hole SH to the sum of the force values of the force sensor 400 may vary according to the magnitude of the force applied to the force sensor 400. In FIG. 32, an X-axis represents the force (gram-force (gf)) applied by the object, and a Y-axis represents the ratio of the force value of the sensor hole SH in the force sensor 400 including the sensor hole SH to the sum of the force values of the force sensor 400' not including the sensor hole SH. Therefore, the sum of the force values calculated from the force sensor 400 including the sensor hole SH and the force value of the sensor hole SH may be calculated according to the magnitude of the force applied to the force sensor 400 and stored in a lookup table.

In a force sensor and a display device including the same according to an embodiment, light emitted from a light emitting unit can be absorbed by or reflected from blood vessels of a user's finger after passing through a sensor hole of the force sensor and a through hole of a display panel. The light reflected from the blood vessels of the user's finger can be sensed by an optical sensor after passing through the through hole of the display panel and the sensor hole of the force sensor.

In a force sensor and a display device including the same according to an embodiment, although a first sub-force sensor electrode and a second sub-force sensor electrode are disconnected by the sensor hole, the first sub-force sensor electrode and the second sub-force sensor electrode may be respectively connected to sub-force sensor wirings, so that the first and second sub-force sensor electrodes can be electrically connected to a force driving unit.

In a force sensor and a display device including the same according to an embodiment, although the first sub-force sensor electrode and the second sub-force sensor electrode are disconnected by the sensor hole, the first and second sub-force sensor electrodes can be electrically connected through a sensor connection wiring.

In a force sensor and a display device including the same according to an embodiment, a force sensor electrode is removed from the sensor hole, but a force value of the sensor hole can be calculated using force values of force sensing cells.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A force sensor comprising:
a first base substrate and a second base substrate facing each other;
first force sensor electrodes extending in a first direction and arranged in a second direction crossing the first direction on the first base substrate;
second force sensor electrodes extending in the second direction and arranged in the first direction on the second base substrate; and
a sensor hole configured to transmit light,
wherein any one of the first force sensor electrodes includes a first sub-force sensor electrode disposed on a first side of the sensor hole and a second sub-force sensor electrode disposed on a second side opposite to the first side of the sensor hole,
wherein any one of the second force sensor electrodes includes a third sub-force sensor electrode disposed on a third side of the sensor hole and a fourth sub-force sensor electrode disposed on a fourth side opposite to the third side of the sensor hole, and
wherein the sensor hole is between the first sub-force sensor electrode and the second sub-force sensor electrode in the first direction in plan view, and the sensor hole is between the third sub-force sensor electrode and the fourth sub-force sensor electrode in the second direction in plan view.

2. The force sensor of claim 1, further comprising:
a first sub-force sensor wiring disposed on the first base substrate and connected to a first side end of the first sub-force sensor electrode; and
a second sub-force sensor wiring disposed on the first base substrate and connected to a second side end of the second sub-force sensor electrode.

3. The force sensor of claim 2, further comprising:
a first sub-force sensor pad and a second sub-force sensor pad disposed on the first base substrate and connected to the first sub-force sensor wiring and the second sub-force sensor wiring, respectively.

4. The force sensor of claim 2, further comprising:
a third sub-force sensor wiring disposed on the second base substrate and connected to a third side end of the third sub-force sensor electrode; and
a fourth sub-force sensor wiring disposed on the second base substrate and connected to a fourth side end of the fourth sub-force sensor electrode.

5. The force sensor of claim 4, further comprising:
a first sub-force sensor pad and a second sub-force sensor pad disposed on the first base substrate and connected to the first sub-force sensor wiring and the second sub-force sensor wiring, respectively; and a third sub-force sensor pad and a fourth sub-force sensor pad disposed on the second base substrate and connected to the third sub-force sensor wiring and the fourth sub-force sensor wiring, respectively.

6. The force sensor of claim 1, further comprising:
a first force connection wiring disposed on the first base substrate and configured to bypass the sensor hole to connect the first sub-force sensor electrode to the second sub-force sensor electrode.

7. The force sensor of claim 6, further comprising:
a second force connection wiring disposed on the second base substrate and configured to bypass the sensor hole to connect the third sub-force sensor electrode to the fourth sub-force sensor electrode.

8. The force sensor of claim 1, wherein each of a length of the first sub-force sensor electrode in the first direction and a length of the second sub-force sensor electrode in the second direction is smaller than a length of any one of remaining first force sensor electrodes other than the first force sensor electrode in the first direction.

9. The force sensor of claim 1, wherein each of a length of the third sub-force sensor electrode in the second direction and a length of the fourth sub-force sensor electrode in the second direction is smaller than a length of any one of remaining first force sensor electrodes other than the second force sensor electrode in the second direction.

10. The force sensor of claim 1, wherein a length of one of the second force sensor electrodes that is disposed on a third side of the sensor hole, in the second direction, among the second force sensor electrodes, is smaller than a length of any other one of the second force sensor electrodes in the second direction.

11. The force sensor of claim 1, further comprising:
force sensitive layers disposed between the first force sensor electrodes and the second force sensor electrodes, respectively, in a thickness direction of the first base substrate.

12. The force sensor of claim 11, wherein each of the force sensitive layers is in contact with at least one of any one of the first force sensor electrodes or any one of the second force sensor electrodes.

13. The force sensor of claim 1, wherein the sensor hole passes through the first base substrate and the second base substrate.

14. The force sensor of claim 13, wherein the first force sensor electrodes and the second force sensor electrodes are not disposed in the sensor hole.

15. A display device comprising:
a display panel including a display area having pixels configured to display an image;
a force sensor disposed on one surface of the display panel to sense a force applied from an outside, and including a sensor hole which transmits light in a thickness direction of the display panel; and
an optical sensor disposed to overlap the sensor hole in the thickness direction of the display panel and configured to sense light incident through the sensor hole,
wherein the force sensor includes a first force sensor electrode and a first sub-force sensor electrode disposed on a first side of the sensor hole and a second sub-force sensor electrode disposed on a second side opposite to the first side of the sensor hole, and
wherein the force sensor overlaps the display area of the display panel in the thickness direction.

16. The display device of claim 15, further comprising:
a bottom panel cover disposed on one surface of the force sensor and including a cover hole disposed to overlap the sensor hole in the thickness direction of the display panel.

17. The display device of claim 16, wherein a size of the cover hole is larger than a size of the sensor hole.

18. The display device of claim 15, further comprising:
a bracket disposed on one surface of the force sensor and including a battery hole disposed to overlap the sensor hole in the thickness direction of the display panel.

19. The display device of claim 18, wherein a size of the battery hole is larger than a size of the sensor hole.

20. The display device of claim 18, wherein the optical sensor is disposed in the battery hole.

21. The display device of claim 15, further comprising:
a light emitting unit disposed to overlap the sensor hole in the thickness direction of the display panel and configured to emit light.

22. The display device of claim 15, wherein the display panel further includes a through hole disposed to overlap the sensor hole in the thickness direction of the display panel.

23. The display device of claim 22, wherein a size of the through hole is smaller than a size of the sensor hole.

24. The display device of claim 15, wherein the display area includes a main display area and a sub-display area overlapping the sensor hole in the thickness direction of the display panel, and
wherein the number of pixels per unit area of the main display area is greater than the number of pixels per unit area of the sub-display area.

25. The display device of claim 24, wherein the sub-display area includes a pixel area in which the pixels are disposed and a transmission area disposed on at least one side of the pixel area.

26. The display device of claim 15, further comprising:
a main circuit board having the optical sensor disposed on one surface thereof; and
a main processor or main connector disposed on the other surface opposite to the one surface of the main circuit board.

27. The display device of claim 26, further comprising:
a display circuit board attached to one side of the display panel; and
a cable connecting the display circuit board to the main connector.

28. The display device of claim 15, wherein the force sensor includes:
a first base substrate and a second base substrate facing each other, wherein the first force sensor electrodes extend in a first direction and are arranged in a second direction crossing the first direction on the first base substrate; and
second force sensor electrodes extending in the second direction and arranged in the first direction on the second base substrate.

29. A method of driving a force sensor, the method comprising:
applying driving signals to the first force sensor electrodes, and detecting sensing signals from the second force sensor electrodes;
analyzing the sensing signals to calculate force values of force sensing cells disposed in crossing regions of the first force sensor electrodes and the second force sensor electrodes, respectively; and
calculating a force value of the sensor hole using the force values, wherein the calculating the force value of the sensor hole using the force values comprises:

calculating the force value of the sensor hole using a lookup table storing the force value of the sensor hole according to the sum of the force values.

30. The method of claim 29, wherein the calculating the force value of the sensor hole using the force values comprises:

calculating the force value of the sensor hole stored in the lookup table by subtracting the sum of force values calculated from the force sensor including the sensor hole from the sum of force values calculated from the force sensor not including the sensor hole.

* * * * *